US010252035B2

(12) United States Patent
Aggerholm et al.

(10) Patent No.: US 10,252,035 B2
(45) Date of Patent: Apr. 9, 2019

(54) ROTATABLE CONTROL HANDLES FOR MEDICAL DEVICES AND METHODS OF USING ROTATABLE CONTROL HANDLES

(71) Applicants: Steen Aggerholm, St. Heddinge (DK); Kirsten Asser Larsen, Moerkoev (DK)

(72) Inventors: Steen Aggerholm, St. Heddinge (DK); Kirsten Asser Larsen, Moerkoev (DK)

(73) Assignee: Cook Medical Techonologies LLC, Bloomington, IN (US)

( * ) Notice: Subject to any disclaimer, the term of this patent is extended or adjusted under 35 U.S.C. 154(b) by 221 days.

(21) Appl. No.: 15/368,724

(22) Filed: Dec. 5, 2016

(65) Prior Publication Data
US 2017/0157365 A1 Jun. 8, 2017

Related U.S. Application Data

(60) Provisional application No. 62/263,904, filed on Dec. 7, 2015.

(51) Int. Cl.
*A61M 25/09* (2006.01)
*A61B 17/34* (2006.01)
*G05G 1/10* (2006.01)

(52) U.S. Cl.
CPC ... *A61M 25/09041* (2013.01); *A61B 17/3423* (2013.01); *A61B 17/3468* (2013.01); *A61B 17/3476* (2013.01); *A61B 17/3498* (2013.01); *G05G 1/10* (2013.01); *A61M 2025/09116* (2013.01); *G05G 2700/12* (2013.01)

(58) Field of Classification Search
CPC .. A61M 25/09041; A61M 2025/09116; G05G 1/10; G05G 2700/12; A61B 17/3423; A61B 17/3498; A61B 17/3476; A61B 17/3468
See application file for complete search history.

(56) References Cited

U.S. PATENT DOCUMENTS

| 4,215,871 A | 8/1980 | Hirsch et al. |
| 4,589,415 A | 5/1986 | Haaga |
| 4,721,107 A | 1/1988 | Bolg et al. |
| 4,726,369 A | 2/1988 | Mar |

(Continued)

FOREIGN PATENT DOCUMENTS

| EP | 1378261 | 1/2004 |
| EP | 1528893 | 7/2009 |

(Continued)

OTHER PUBLICATIONS

European Patent Office, Extended European Search Report, dated Nov. 5, 2017.

(Continued)

*Primary Examiner* — Amber R Stiles
(74) *Attorney, Agent, or Firm* — Buchanan Van Tuinen LLC

(57) ABSTRACT

Rotatable control handles and methods of using rotatable control handles are described herein. An example embodiment of a rotatable control handle comprises a handle, a compressible member disposed within the handle, a cap attached to the handle, and a cannula rotatably attached between the handle and the cap. The handle comprises a first member and a second member that is releasably attachable to the first member.

20 Claims, 7 Drawing Sheets

(56) References Cited

U.S. PATENT DOCUMENTS

| | | | |
|---|---|---|---|
| 4,774,947 A | 10/1988 | Falk et al. |
| 4,823,793 A | 4/1989 | Angulo et al. |
| 4,858,810 A | 8/1989 | Intlekofer et al. |
| 4,960,108 A | 10/1990 | Reichel et al. |
| 5,045,061 A | 9/1991 | Seifert et al. |
| 5,065,761 A | 11/1991 | Pell |
| 5,117,839 A | 6/1992 | Dance |
| 5,137,288 A | 8/1992 | Starkey et al. |
| 5,159,861 A | 11/1992 | Anderson |
| 5,161,534 A | 11/1992 | Berthiaume |
| 5,163,421 A | 11/1992 | Bernstein et al. |
| 5,163,903 A | 11/1992 | Crittenden et al. |
| 5,199,417 A | 4/1993 | Muller et al. |
| 5,219,332 A | 6/1993 | Nelson et al. |
| 5,242,454 A | 9/1993 | Gundlach et al. |
| 5,273,052 A | 12/1993 | Kraus et al. |
| 5,312,418 A | 5/1994 | Bonnet |
| 5,325,868 A | 7/1994 | Kimmelstiel |
| 5,392,778 A | 2/1995 | Horzewski |
| 5,425,735 A | 6/1995 | Rosen et al. |
| 5,484,433 A | 1/1996 | Taylor et al. |
| 5,540,656 A | 7/1996 | Pflueger et al. |
| 5,851,189 A | 12/1998 | Forber |
| 5,868,756 A | 2/1999 | Henry et al. |
| 5,906,623 A | 5/1999 | Peterson |
| 5,954,670 A | 9/1999 | Baker |
| 6,007,560 A | 12/1999 | Gottlieb et al. |
| 6,030,349 A | 2/2000 | Wilson et al. |
| 6,033,414 A | 3/2000 | Tockman et al. |
| 6,217,588 B1 | 4/2001 | Jerger et al. |
| 6,238,389 B1 | 5/2001 | Paddock et al. |
| 6,241,744 B1 | 6/2001 | Imran et al. |
| 6,352,534 B1 | 3/2002 | Paddock et al. |
| 6,440,123 B1 | 8/2002 | Engel |
| 6,458,137 B1 | 10/2002 | Klint |
| 6,482,203 B2 | 11/2002 | Paddock et al. |
| 6,533,772 B1 | 3/2003 | Sherts et al. |
| 6,613,014 B1 | 9/2003 | Chi |
| 6,645,223 B2 | 11/2003 | Boyle et al. |
| 6,660,013 B2 | 12/2003 | Rabiner et al. |
| 7,087,061 B2 | 8/2006 | Chernenko et al. |
| 7,144,378 B2 | 12/2006 | Arnott |
| 7,470,274 B2 | 12/2008 | Lebet |
| 7,717,865 B2 | 5/2010 | Boutillette et al. |
| 7,831,297 B2 | 11/2010 | Opie et al. |
| 7,909,821 B2 | 3/2011 | Paddock et al. |
| 7,972,282 B2 | 7/2011 | Clark et al. |
| 7,993,329 B2 | 8/2011 | *Howell et al. |
| 8,038,628 B2 | 10/2011 | von Malmborg et al. |
| 8,147,481 B2 | 4/2012 | Whittaker et al. |
| 8,496,603 B2 | 7/2013 | Mamourian |
| 9,597,152 B2 | 3/2017 | Schaeffer et al. |
| 2001/0016712 A1 | 8/2001 | Hamilton |
| 2003/0069522 A1 | 4/2003 | Jacobsen et al. |
| 2003/0176873 A1 | 9/2003 | Chernenko et al. |
| 2004/0006329 A1* | 1/2004 | Scheu ............... A61M 25/0113 604/528 |
| 2004/0039372 A1 | 2/2004 | Carmody |
| 2004/0172116 A1 | 9/2004 | Seifert et al. |
| 2004/0215108 A1 | 10/2004 | Windheuser |
| 2004/0225283 A1 | 11/2004 | Nahleili |
| 2005/0070820 A1 | 3/2005 | Boutillette et al. |
| 2005/0288655 A1 | 12/2005 | Root et al. |
| 2006/0229496 A1 | 10/2006 | Windheuser et al. |
| 2007/0004991 A1 | 1/2007 | Shelton |
| 2007/0010849 A1 | 1/2007 | Balgobin et al. |
| 2007/0016166 A1 | 1/2007 | Thistle |
| 2007/0021754 A1 | 1/2007 | Chernenko et al. |
| 2007/0179486 A1 | 8/2007 | Welch et al. |
| 2008/0103481 A1 | 4/2008 | Vogel et al. |
| 2008/0132906 A1 | 6/2008 | Rasmussen |
| 2008/0147110 A1 | 6/2008 | Wijeratne |
| 2008/0312671 A1 | 12/2008 | Riles et al. |
| 2009/0118741 A1 | 5/2009 | Lebet |
| 2009/0124899 A1 | 5/2009 | Jacobs et al. |
| 2009/0124934 A1 | 5/2009 | Rabbitte et al. |
| 2009/0292278 A1 | 11/2009 | Lewinsky et al. |
| 2010/0036294 A1 | 2/2010 | Mantell et al. |
| 2010/0100103 A1 | 4/2010 | Haskal et al. |
| 2010/0211006 A1 | 8/2010 | Schmidt-Sorensen |
| 2011/0112507 A1 | 5/2011 | Linderman et al. |
| 2011/0245841 A1 | 10/2011 | Shohat et al. |
| 2012/0136425 A1 | 5/2012 | Orr |
| 2013/0018359 A1 | 1/2013 | Coyle |
| 2013/0035749 A1 | 2/2013 | Farag |
| 2013/0103001 A1 | 4/2013 | BenMaamer et al. |
| 2013/0237968 A1 | 9/2013 | Schaeffer et al. |
| 2013/0303330 A1 | 11/2013 | Stevens et al. |

FOREIGN PATENT DOCUMENTS

| | | |
|---|---|---|
| EP | 2359776 | 8/2011 |
| WO | WO2005094936 | 10/2005 |
| WO | WO2013036900 | 3/2013 |
| WO | 2015021009 | 2/2015 |
| WO | 2015164284 | 10/2015 |

OTHER PUBLICATIONS

William Cook Europe, "Flipper Detachable Embolization Coil," 2008, Denmark.

Cook Incorporated,"Retracta Detachable Embolization Coils," 2013, Bloomington, Indiana, United States.

European Patent Office, Partial European Search Report, for European Application No. 13160954.7 dated Jun. 6, 2013, p. 1-5.

European Patent Office, Extended European Search Report for application No. 13160954.7 dated Sep. 26, 2013, p. 1-9.

International Searching Authority, The International Search Report and the Written Opinion of the International Searching Authority for International Application No. PCT/US2012/054374 dated Dec. 12, 2012.

* cited by examiner

ROTATABLE CONTROL HANDLES FOR MEDICAL DEVICES AND METHODS OF USING ROTATABLE CONTROL HANDLES

RELATED APPLICATION

This application claims the benefit of U.S. Provisional Application No. 62/263,904, filed Dec. 7, 2015. The entire disclosure of this related application is hereby incorporated into this disclosure by reference.

FIELD

The disclosure relates generally to the field of medical devices and methods of using medical devices. More particularly, the disclosure relates to the field of control handles for medical devices, such as guidewires, and methods of using control handles.

BACKGROUND

Numerous procedures have been developed that require the percutaneous insertion of one or more medical devices into the body of a patient. Such procedures include, for example, percutaneous transluminal coronary angioplasty (PTCA), X-ray angiographic procedures, embolization procedures, and the like. The medical devices intended for use in such procedures may be introduced into the vascular system by a variety of known techniques. For example, in the widely used Seldinger technique, a surgical opening is made in a body vessel, such as an artery or vein, by a needle, and a guidewire is inserted into the body vessel through a bore in the needle. The needle is then withdrawn, leaving the guidewire in place. A dilator positioned within the lumen of an introducer device is then inserted over the guidewire and advanced into the body vessel. Once the introducer is positioned as desired within the body vessel, the dilator is withdrawn. A variety of medical devices, such as catheters, delivery systems, cardiac leads, and the like, can then be advanced through the introducer to a point of treatment in the body vessel. For example, a delivery system that includes a guidewire with an attached embolization coil can be introduced through the introducer to a point of treatment and delivered using conventional techniques (e.g., rotating the guidewire such that the embolization coil becomes free of the guidewire).

In many cases, an introducer will include one or more hemostatic valve members (also referred to as check valves) for inhibiting leakage of bodily fluids, such as blood, through the introducer as a medical device is inserted through or withdrawn from the introducer. In some cases, hemostatic valves that include a valve member, such as an elastomeric member, are used to minimize fluid leakage during these exchanges. Hemostatic valves of this type are dependent upon the ability of the valve member to seal around the interventional devices to close any gaps created upon insertion or withdrawal of the device through the valve.

The introduction and maneuvering of medical devices, such as guidewires, through a valve member of a hemostatic valve present various challenges. For example, when disposed through a valve member, a guidewire can be difficult to introduce and withdraw from the valve member and rotation of the guidewire relative to the valve member can require two hands, which increases the complexity of the procedure. In addition, the manipulation of the guidewire through the valve member sometimes results in the guidewire becoming kinked, which may result in the guidewire becoming unsuitable for continued use throughout the remainder of the procedure. Control handles for guidewires have been developed that can be used during the performance of a procedure. However, these devices fail to provide support for the guidewire through valve members and also fail to provide a mechanism for rotating the guidewire relative to a portion of the control handle when the guidewire is disposed through a valve member. Thus, there is a need for improved rotatable control handles and methods of using rotatable control handles.

BRIEF SUMMARY OF SELECTED EXAMPLE EMBODIMENTS

Rotatable control handles useful for controlling the position of a medical device are provided. An example rotatable control handle comprises a handle, a compressible member, a cap, and a cannula. The handle has a first member and a second member that is releasably attached to the first member. The handle is moveable between a first configuration in which the first member is free of attachment to the second member and a second configuration in which the first member is releasably attached to the second member. The compressible member is partially disposed within the first member and the second member and is movable between a first configuration when the handle is in the first configuration and a second configuration when the handle is in the second configuration. The compressible member has a compressible member first end, a compressible member second end, and a compressible member body that defines a base and a plurality of arms. The plurality of arms extends from the base and cooperatively defines a first inside diameter when the compressible member is in the first configuration and a second inside diameter when the compressible member is in the second configuration. The second inside diameter is less than the first inside diameter. The cap is attached to the handle and has a cap first end, a cap second end, and a cap body that defines a cap recess and a cap passageway. The cap recess extends into the cap body from the cap first end toward the cap second end. The cap passageway extends from the cap second end to the cap recess and is in communication with the cap recess. The cannula is rotatably attached to the cap and is partially disposed within the cap recess and between the second member and the cap. The cannula is disposed through the cap passageway and has a cannula first end, a cannula second end, and a cannula body that defines a cannula passageway that extends from the cannula first end to the cannula second end.

Another example rotatable control handle comprises a handle, a compressible member, a cap, a guide member, and a cannula. The handle has a first member and a second member that is releasably attached to the first member. The handle is moveable between a first configuration in which the first member is free of attachment to the second member and a second configuration in which the first member is releasably attached to the second member. The first member has a first member first end, a first member second end, and a first member body that defines a first member passageway and a first member recess. The first member passageway extends from the first member first end toward the first member second end. The first member recess extends from the first member second end toward the first member first end and is in communication with the first member passageway. The second member has a second member first end, a second member second end, and a second member body that defines a second member first recess, a second member second recess, and a second member passageway. The second member first recess extends from the second member first end toward the second member second end. The second member second recess extends from the second member second end toward the second member first end. The second member passageway extends from the second member first recess to the second member second recess and is in communication with the second member first recess and second member second recess. The compressible member is partially disposed within the first member recess and the second member first recess and is movable between a first configuration when the handle is in the first configuration and a second configuration when the handle is in the second configuration. The compressible member has a compressible member first end, a compressible member second end, and a compressible member body that defines a base and a plurality of arms. The plurality of arms extends from the base and cooperatively defines a first inside diameter when the compressible member is in the first configuration and a second inside diameter when the compressible member is in the second configuration. The second inside diameter is less than the first inside diameter. The cap is attached to the handle and has a cap first end, a cap second end, and a cap body that defines a cap recess and a cap passageway. The cap recess extends into the cap body from the cap first end toward the cap second end. The cap passageway extends from the cap second end to the cap recess and is in communication with the cap recess. The guide member is disposed between the second member and the cap and has a guide member first end, a guide member second end, and a guide member body that defines a guide member passageway. The guide member passageway extends from the guide member first end to the guide member second end. The cannula is rotatably attached to the cap and is partially disposed within the cap recess and between the second member and the guide member. The cannula is disposed through the cap passageway and has a cannula first end, a cannula second end, and a cannula body that defines a cannula passageway that extends from the cannula first end to the cannula second end.

Another example rotatable control handle comprises a handle, a compressible member, a cap, a guide member, and a cannula. The handle has a first member and a second member that is releasably attached to the first member. The handle is moveable between a first configuration in which the first member is free of attachment to the second member and a second configuration in which the first member is releasably attached to the second member. The first member has a first member first end, a first member second end, and a first member body that defines a first member passageway and a first member recess. The first member passageway extends from the first member first end toward the first member second end. The first member recess extends from the first member second end toward the first member first end and is in communication with the first member passageway. The second member has a second member first end, a second member second end, and a second member body that defines a second member first recess, a second member second recess, and a second member passageway. The second member first recess extends from the second member first end toward the second member second end. The second member second recess extends from the second member second end toward the second member first end. The second member passageway extends from the second member first recess to the second member second recess and is in communication with the second member first recess and second member second recess. The compressible member is partially disposed within the first member recess and the second member first recess and is movable between a first configuration when the handle is in the first configuration and a second configuration when the handle is in the second configuration. The compressible member has a compressible member first end, a compressible member second end, and a compressible member body that defines a base, a first arm that extends from the base, a second arm that extends from the base, a third arm that extends from the base, and a fourth arm that extends from the base. The compressible member body defines a projection and a notch on each of the first arm, the second arm, the third arm, and the fourth arm. The first arm, the second arm, the third arm, and the fourth arm cooperatively define a first inside diameter when the compressible member is in the first configuration and a second inside diameter when the compressible member is in the second configuration. The second inside diameter is less than the first inside diameter. The notch defined on the first arm is disposed a first distance from the compressible member second end. The projection defined on the first arm is disposed a second distance from the compressible member second end that is different than the first distance. The cap is attached to the handle and has a cap first end, a cap second end, and a cap body that defines a cap recess and a cap passageway. The cap recess extends into the cap body from the cap first end toward the cap second end. The cap passageway extends from the cap second end to the cap recess and is in communication with the cap recess. The guide member is disposed between the second member and the cap and has a guide member first end, a guide member second end, and a guide member body that defines a guide member passageway. The guide member passageway extends from the guide member first end to the guide member second end and has a third inside diameter and a fourth inside diameter that is less than the third inside diameter. The cannula is rotatably attached to the cap and is partially disposed within the cap recess and between the second member and the guide member. The cannula is disposed through the cap passageway and has a cannula first end, a cannula second end, and a cannula body that defines a cannula passageway that extends from the cannula first end to the cannula second end.

Methods of using a rotatable control handle are also provided. An example method of using a rotatable control handle comprises the steps of: positioning a rotatable control handle on a medical device having a medical device first end and a medical device second end; moving the handle of the rotatable control handle from a first configuration to a second configuration; applying an axial force on the rotatable control handle directed toward a valve device having a housing and a valve member such that the medical device is advanced through the valve member of the valve device and the first end of the medical device is disposed on a first side of the valve member and the second end of the medical device is disposed on a second side of the valve member; continuing the application of an axial force on the rotatable control handle such that the rotatable control handle and the medical device are advanced through the valve member of the valve device and the first end of the cannula of the rotatable control handle is disposed on the second side of the valve member and the second end of the cannula is disposed on the first side of the valve member; applying torque to the handle of the rotatable control handle such that the handle and medical device rotate relative to the valve device; moving the handle of the rotatable control handle from a second configuration to a first configuration; applying axial force on the medical device such that the medical device moves relative to the handle; moving the handle of the rotatable control handle from the first configuration to the second configuration; applying an axial force on the rotatable control handle directed away from the valve device such that the rotatable control handle and the medical device are withdrawn from the valve member of the valve device, the second end of the cannula of the rotatable control handle is disposed on the second side of the valve member, and the medical device and rotatable control handle are free of the valve device.

Additional understanding of the exemplary rotatable control handles and methods of using rotatable control handles can be obtained by review of the detailed description, below, and the appended drawings.

DETAILED DESCRIPTION

Figure 1:
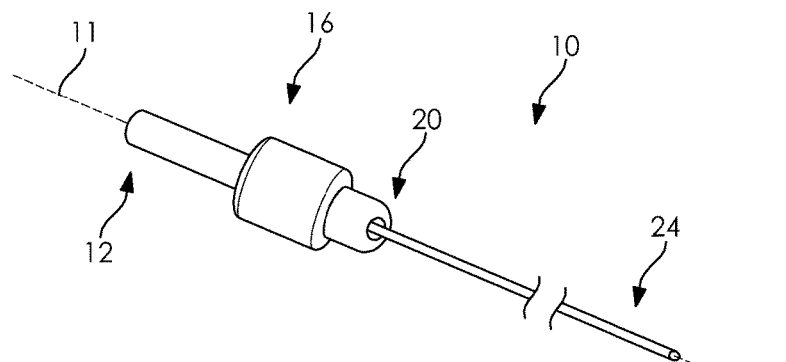
FIG. 1 is a perspective view of an example embodiment of a rotatable control handle.
Figure 2:
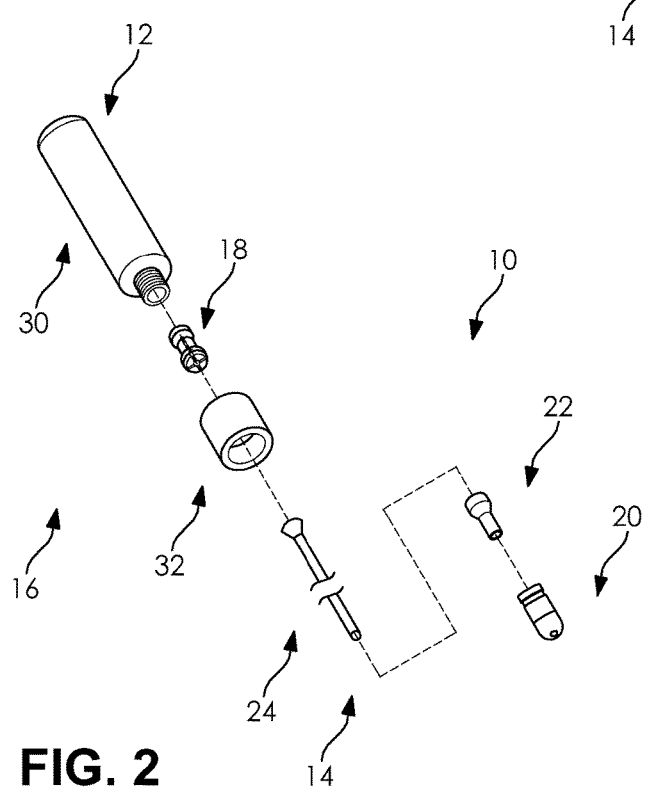
FIG. 2 is an exploded view of the rotatable control handle illustrated in FIG. 1.
Figure 3:
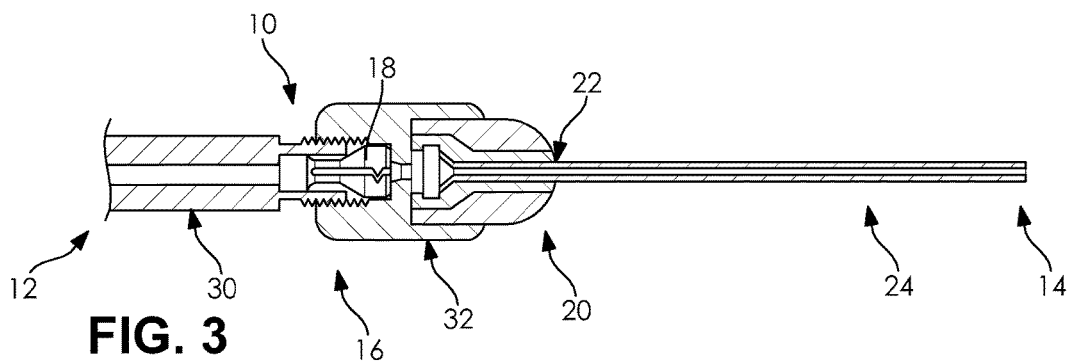
FIG. 3 is a partial sectional view of the rotatable control handle illustrated in FIG. 1 taken along the lengthwise axis of the rotatable control handle.

The following detailed description and the appended drawings describe and illustrate various example embodiments of a rotatable control handle that can be used with various medical devices and methods of using a rotatable control handle. The description and illustration of these examples are provided to enable one skilled in the art to make and use a rotatable control handle and to practice a method of using a rotatable control handle. They are not intended to limit the scope of the claims in any manner.

The use of "e.g.," "example," and "or," and grammatically related terms, indicate non-exclusive alternatives without limitation, unless otherwise noted. The term "diameter" refers to the length of a straight line passing from side to side through the center of a body, element, or feature, and does not impart any structural configuration on the body, element, or feature. The recitation of a first structural feature "circumferentially adjacent" to a second structural feature means that the first structural feature is the nearest first structural feature to the second structural feature when moving along an imaginary line that extends from the first structural feature to the second structural feature.

FIGS. 1, 2, 3, 4, 5, 5A, 5B, 5C, 5D, 6, 7, and 8 illustrate a rotatable control handle 10 for use on a medical device, such as a guidewire. The control handle 10 has a lengthwise axis 11, a first end 12, a second end 14, and comprises a handle 16, a compressible member 18, a cap 20, a guide member 22, and a cannula 24.

Figure 4:
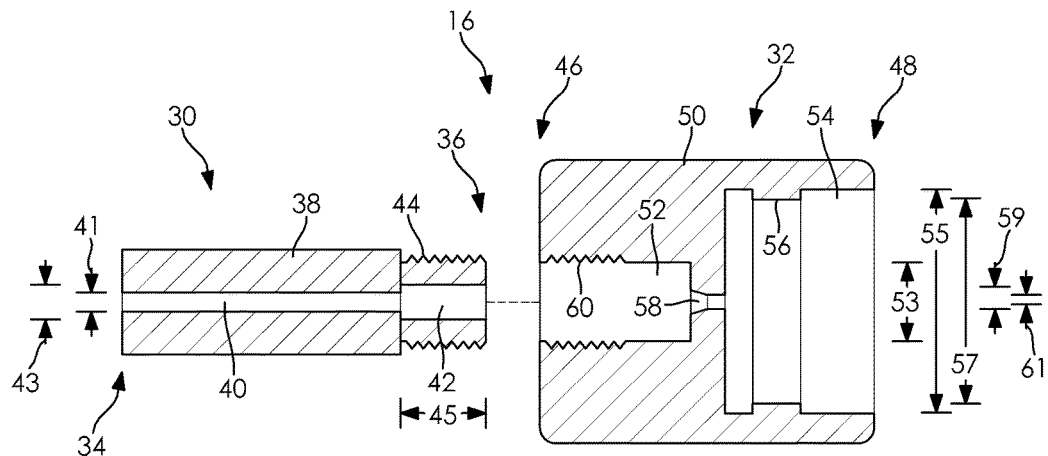
FIG. 4 is an exploded sectional view of the handle of the rotatable control handle illustrated in FIG. 1 taken along the lengthwise axis of the handle.

As illustrated in FIG. 4, the handle 16 has a first member 30 that is releasably attachable to a second member 32. The handle 16 is moveable between a first configuration in which the first member 30 is free of attachment to the second member 32, and a second configuration in which the first member 30 is releasably attached to the second member 32. The first member 30 has a first end 34, a second end 36, and a body 38 that defines a passageway 40, a recess 42, and threads 44. The passageway 40 extends through a portion of the body 38 and from the first end 34 toward the second end 36 of the first member 30 and is in communication with the recess 42. The passageway 40 has a passageway diameter 41 that is sized and configured to receive a medical device, such as a guidewire. The recess 42 extends into the body 38 from the second end 36 toward the first end 34 of the first member 30. The recess 42 has a recess diameter 43 and a length 45 that is sized and configured to house a portion of the compressible member 18, as described in more detail herein. The recess diameter 43 is greater than the passageway diameter 41. The threads 44 extend from the second end 36 toward the first end 32 and are sized and configured to mate with the threads 60 defined by the second member 32 of the handle 16, as described in more detail herein.

The second member 32 of the handle 16 is releasably attachable to the first member 30 when the handle 16 is in the second configuration. As illustrated in FIG. 1, the second member 32 is releasably attached to the first member 30. The second member 32 has a first end 46, a second end 48, and a body 50 that defines a first recess 52, a second recess 54, a projection 56, a passageway 58, and threads 60. In the illustrated embodiment, the second member 32 has a length that extends from the first end 46 to the second end 48 that is equal to about 18 millimeters and has a diameter at the first end 46 that is equal to about 14.5 millimeters. The first recess 52 extends into the body 50 from the first end 46 toward the second end 48 and has a first recess diameter 53 that is sized and configured to receive a portion of the first member 30 and a portion of the compressible member 18. In the illustrated embodiment, the first recess diameter 53 is equal to about 6.35 millimeters and has a length that extends from the first end 46 to the passageway 58 that is equal to about 8 millimeters. The first recess 52 is in communication with the passageway 58. The second recess 54 extends into the body 50 from the second end 48 toward the first end 46 and has a second recess diameter 55 that is greater than the first recess diameter 53 and is sized and configured to receive a portion of the cap 20, guide member 22, and cannula 24. In the illustrated embodiment, the second recess diameter 55 is equal to about 11 millimeters and has a length that extends from the second end 48 to the passageway 58 that is equal to about 8 millimeters. The second recess 54 is in communication with the passageway 58. The projection 56 extends into the second recess 54 and toward the lengthwise axis of the second member 32 and defines a projection diameter 57 within the second recess 54 that is less than the second recess diameter 55. The projection 56 provides structure for rotatably attaching the cap 20 to the handle 16, as described in more detail herein. In the illustrated embodiment, the projection diameter 57 is equal to about 10.3 millimeters. The passageway 58 extends through a portion of the body 50 of the second member 32 and from the first recess 52 to the second recess 54 such that the passageway 58 is in communication with each of the first recess 52 and the second recess 54. The passageway 58 has a first passageway diameter 59 at the opening in communication with the first recess 52 and a second passageway diameter 61 at the opening in communication with the second recess 54. The first passageway diameter 59 is greater than the second passageway diameter 61. In the illustrated embodiment, the second passageway diameter 61 is equal to about 1.1 millimeters. The diameter of the passageway 58 tapers from the first passageway diameter 59 to the second passageway diameter 61 along a first portion of the length of the passageway 58 that extends from the first recess 52 toward the second recess 54 such that the wall of the passageway 58 along the first portion of the length of the passageway 58 is disposed at an angle equal to about 30 degrees relative to the lengthwise axis of the second member 32. The passageway 58 is sized and configured to receive a medical device, such as a guidewire. In the illustrated embodiment, the first portion of the passageway 58 has a length that extends from the first recess 52 to a second portion of the passageway that is equal to about 0.9 millimeters.

While the handle 16 has been illustrated as having a particular structural configuration and having particular dimensions, a handle included in a rotatable control handle can have any suitable structural configuration and can have any suitable dimensions. Selection of a suitable structural configuration and dimensions for a handle can be based on various considerations, such as the structural configuration of a compressible member included in the rotatable control handle and/or the material(s) that forms the medical device on which the handle is intended to be disposed. For example, the first member and/or second member of a handle can define one or more recesses and/or projections on an exterior surface that are sized and configured to provide tactile feedback as to the movement of the member during use. Alternative to the configuration illustrated in FIGS. 1, 2, 3, and 4, a handle can omit the inclusion of the projection and/or the handle included in a rotatable control handle can define a compressible member (e.g., collet) such that the handle can be directly attached to a medical device, such as a guidewire, without the inclusion of a separate component (e.g., compressible member 18).

While the first member 30 has been illustrated as being attached to the second member 32 using a threaded connection, a first member can be releasably attached to a second member using any technique or method of attachment considered suitable for a particular embodiment. Selection of a suitable technique or method of attachment between a first member and a second member can be based on various considerations, such as the material(s) that forms a first member to which a second member is intended to be attached. Examples of techniques and methods of attachment considered suitable between a first member and a second member include snap fit configurations, threaded connections, and any other technique or method of attachment considered suitable for a particular embodiment. For example, alternative to the first member defining threads on an exterior surface and the second member defining threads within a recess, a first member can define threads within a recess that are sized and configured to mate with threads defined on an exterior surface of a second member. In this alternative configuration, the first member defines a recess sized and configured to receive a portion of the second member and a portion of the compressible member and the second member defines a recess that is sized and configured to receive a portion of the compressible member.

Figure 5:
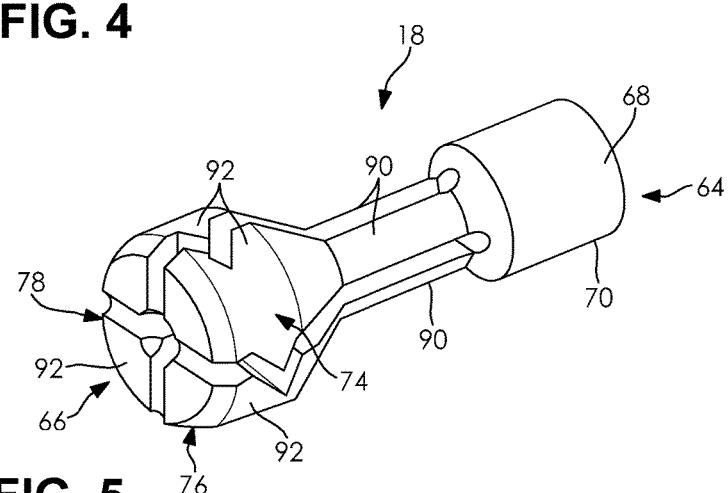
FIG. 5 is a perspective view of the compressible member of the rotatable control handle illustrated in FIG. 1. The compressible member is in a first configuration.
Figures 5A, 5B:
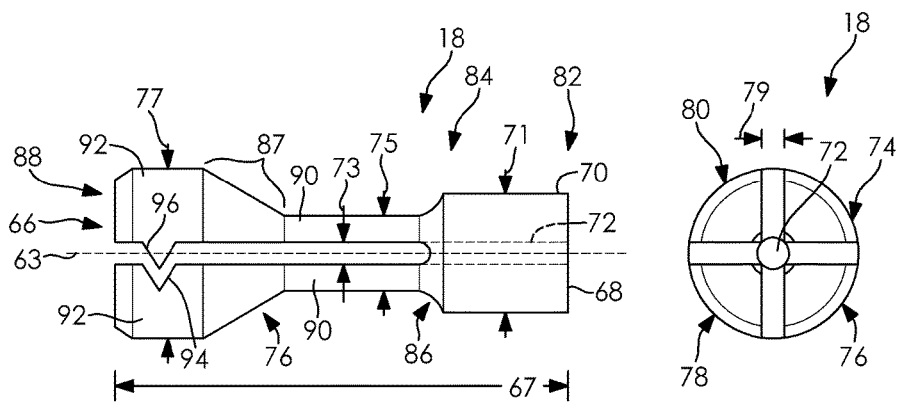
FIG. 5A is an elevation view of the compressible member illustrated in FIG. 5. The compressible member is in a first configuration.
FIG. 5B is an end view of the second end of the compressible member illustrated in FIG. 5. The compressible member is in a first configuration.
Figure 5C:
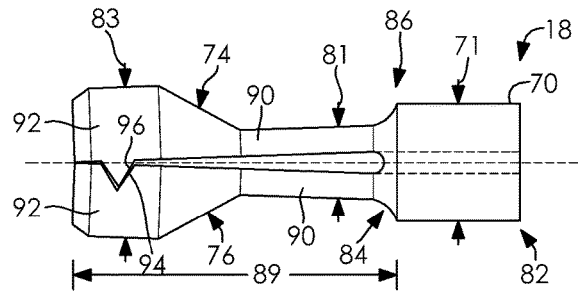
FIG. 5C is an elevation view of the compressible member illustrated in FIG. 5. The compressible member is in a second configuration.
Figure 5D:
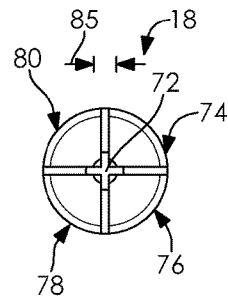
FIG. 5D is an end view of the second end of the compressible member illustrated in FIG. 5. The compressible member is in a second configuration.

In the illustrated embodiment, the compressible member 18 has a lengthwise axis 63, a first end 64, a second end 66, a length 67, and a body 68 that defines a base 70, a passageway 72, a first arm 74, a second arm 76, a third arm 78, and a fourth arm 80. The compressible member 18 is moveable between a first configuration, as shown in FIGS. 5, 5A, and 5B, and a second configuration, as shown in FIGS. 5C and 5D. The compressible member 18 is in the first configuration when the handle 16 is in the first configuration and the compressible member 18 is in the second configuration when the handle 16 is in the second configuration. The length 67 of the compressible member 18 extends from the first end 64 to the second end 66 and is greater than the length 45 of the recess 42 defined by the first member 30. The base 70 has an outside diameter 71, a first end 82, and a second end 84. The outside diameter 71 of the base 70 is sized and configured to be received by the recess 42 defined by the first member 30. The passageway 72 extends through the base 70 from a first opening defined on the first end 82 of the base 70 to a second opening defined on the second end 84 of the base 70. The passageway 72 is sized and configured to receive a medical device, such as a guidewire, and, when the rotatable medical device 10 is assembled as illustrated in FIG. 1, is coaxial with the passageway 40 defined by the first member 30 and the passageway 58 defined by the second member 32.

Each of the arms 74, 76, 78, 80 extends from the base 70 to the second end 66 of the compressible member 18 and is moveable between a first position, as illustrated in FIGS. 5, 5A, and 5B, and a second position, as illustrated in FIGS. 5C and 5D. Each of the arms 74, 76, 78, 80 is in the first position when the compressible member 18 is in the first configuration and each of the arms 74, 76, 78, 80 is in the second position when the compressible member 18 is in the second configuration. Each of the arms 74, 76, 78, 80 has a first end 86 attached to the base 70, a second end 88, a length 89, a shaft 90, and a head 92. The length 89 extends from the first end 86 to the second end 88 and, in the illustrated embodiment, is equal to about 8.8 millimeters. The shaft 90 extends from a first end attached to the base 70 to a second end attached to the head 92 such that the shaft 90 is disposed between the base 70 and the head 92. The head 92 extends from the shaft 90 to the second end 66 of the compressible member 18. The body 68 of the compressible member 18 defines a notch 94 and a projection 96 on the head 92 of each of the arms 74, 76, 78, 80. The notch 94 of each arm 74, 76, 78, 80 is sized and configured to receive a projection of a circumferentially adjacent arm when the compressible member 18 is in the second configuration, as illustrated in FIGS. 5C and 5D. In the illustrated embodiment, the notch 94 is a triangular prismatic notch that extends into the arm a length equal to about 0.9 millimeters and the projection 96 is a triangular prismatic projection that extends from the arm a length equal to about 0.7 millimeters. The notch 94 is positioned on a first side of the head 92 and the projection 96 is positioned on a second side of the head 92 such that a portion of the notch 94 is disposed on a first plane and a portion of the projection 96 is disposed on a second plane that is positioned orthogonal to the first plane. In the illustrated embodiment, when the compressible member 18 is in the first configuration, the projection 96 is partially disposed in the notch 94 of a circumferentially adjacent arm a length equal to about 0.1 millimeters.

In the illustrated embodiment, the first arm 74 defines the notch 94 a first distance from the second end 66 of the compressible member 18 and the projection 96 a second distance from the second end 66 of the compressible member 18 that is greater than the first distance. The second arm 76 defines the notch 94 a third distance from the second end 66 of the compressible member 18 and the projection 96 a fourth distance from the second end 66 of the compressible member 18 that is less than the third distance. The third distance is equal to the second distance. The third arm 78 defines the notch 94 a fifth distance from the second end 66 of the compressible member 18 and the projection 96 a sixth distance from the second end 66 of the compressible member 18 that is greater than the third distance. The fifth distance is equal to the fourth distance. The fourth arm 80 defines the notch 94 a seventh distance from the second end 66 of the compressible member 18 and the projection 96 an eighth distance from the second end 66 of the compressible member 18 that is less than the third distance. The seventh distance is equal to the sixth distance and the eighth distance is equal to the first distance. In the illustrated embodiment, the first distance, the fourth distance, the fifth distance, and the eighth distance are equal to one another and equal to about 1.22 millimeters and the second distance, third distance, sixth distance, and seventh distance are equal to one another and equal to about 1.82 millimeters. While the notch and projection of each arm have been described as being disposed at different distances from the second end of the compressible member, a compressible member can alternatively define a notch and projection at equal distances from the second end of the compressible member.

The first arm 74 is circumferentially adjacent to the second arm 76 and the fourth arm 80. The second arm 76 is circumferentially adjacent to the first arm 74 and the third arm 78. The third arm 78 is circumferentially adjacent to the second arm 76 and the fourth arm 80. The fourth arm 80 is circumferentially adjacent to the third arm 78 and the first arm 74. As illustrated in FIG. 5A, each of the arms 74, 76, 78, 80 is separated from a circumferentially adjacent arm a distance 73 when the compressible member 18 is in the first configuration. In the illustrated embodiment, the distance 73 between each arm when the compressible member 18 is in the first configuration is equal to about 0.6 millimeters and the end of the slot formed between each arm has a radius of curvature equal to about 0.3 millimeters. The arms 74, 76, 78, 80 cooperatively define a first outside diameter 75, a second outside diameter 77, and a first inside diameter 79 when the compressible member 18 is in the first configuration. The first outside diameter 75 is disposed along the length of the shafts 90 and is measured on a plane that is orthogonal to the lengthwise axis 63 of the compressible member 18. The second outside diameter 77 is disposed along the length of the heads 92 and is measured on a plane that is orthogonal to the lengthwise axis 63 of the compressible member 18. The first outside diameter 75 is less than the second outside diameter 77 and is sized and configured to be received by the recess 42 defined by the first member 30. The second outside diameter 77 is greater than the first outside diameter 75 and is less than the diameter 53 of the first recess 52 defined by the second member 32 such that the second end 66 of the compressible member 18 is sized and configured to be received by the first recess 52 defined by the second member 32. The second outside diameter 77 is greater than the diameter 43 of the recess 42 defined by the first member 30. The outside diameter of the compressible member 18 tapers from the second outside diameter 77 to the first outside diameter 75 along a portion 87 of the length 67 of the compressible member 18. This structural configuration provides a mechanism for moving the compressible member 18 between its first configuration when the first member 30 of the handle 16 is free of the second member 32 of the handle 16 and its second configuration when the first member 30 of the handle 16 is releasably attached to the second member 32 of the handle 16. The first inside diameter 79 is measured on a plane that is orthogonal to the lengthwise axis 63 and is sized and configured to receive a medical device, such as a guidewire, and allow a portion of the medical device to pass through the passageway 72.

The arms 74, 76, 78, 80 cooperatively define a third outside diameter 81, a fourth outside diameter 83, and a second inside diameter 85 when the compressible member 18 is in the second configuration, as illustrated in FIGS. 5C and 5D. In use, the compressible member 18 is in the second configuration when it is disposed within the handle 16 and the first member 30 is attached to the second member 32. The third outside diameter 81 is disposed along the length of the shafts 90 and is measured on a plane that is orthogonal to the lengthwise axis 63. The fourth outside diameter 83 is disposed along the length of the heads 92 and is measured on a plane that is orthogonal to the lengthwise axis 63. The third outside diameter 81 is less than the first outside diameter 75. The fourth outside diameter 83 is greater than the third outside diameter 81 and is less than the second outside diameter 77. The fourth outside diameter 83 is greater than the diameter 43 of the recess 42 defined by the first member 30 such that when the compressible member 18 is in the second configuration a portion of the head 92 of each arm is disposed outside of the recess 42 defined by the first member 30. The second inside diameter 85 is measured on a plane that is orthogonal to the lengthwise axis 63 and is sized and configured to receive a portion of a medical device, such as a guidewire, such that the compressible member 18 contacts the medical device along a portion of the shafts 90 and/or heads 92 and the medical device is releasably attached to the compressible member 18 and the handle 16.

In use, the first end 64 of the compressible member 18 is partially positioned within the recess 42 defined by the first member 30 and the second end 66 of the compressible member 18 is advanced into the first recess 52 defined by the second member 32 of the handle 16. The threads 44 of the first member 30 are mated with the threads 60 of the second member 32 such that the application of torque on the first member 30 while the position of the second member 32 is maintained, or vice versa, advances the second end 36 of the first member 30 toward the second end 48 of the second member 32. Alternatively, torque can be applied to both the first member 30 and the second member 32 such that the second end 36 of the first member 30 is advanced toward the second end 48 of the second member 32. This results in the handle 16 moving from the first configuration to the second configuration and the exterior surface of the tapered portion 87 of the compressible member 18 contacting the first end 34 of the first member 30 such that continued advancement of the first member 30 into the second member 32 moves the compressible member 18 from the first configuration to the second configuration.

While the compressible member 18 has been illustrated as a separate component releasably attached to the handle 16, a portion of a handle of a rotatable control handle can alternatively form a compressible member. For example, each arm of a compressible member can be formed by a first member or second member of a handle and adapted to move between first and second configurations, as described herein. In addition, while the compressible member 18 has been illustrated as having a particular structural configuration and particular dimensions, a compressible member included in a rotatable control handle can have any suitable structural configuration and can have any suitable dimensions. Selection of a suitable structural configuration and dimensions for a compressible member can be based on various considerations, such as the structural configuration of the medical device intended to be used with the rotatable control handle. For example, a compressible member can define a curved, rounded, or blunt surface that is directed toward the lengthwise axis of the compressible member such that damage to any medical device disposed through a rotatable control handle can be prevented during use. In addition, while the compressible member 18 has been illustrated as having a first end 64 disposed within the first member 30 of a handle 16 and a second end 66 disposed within the second member 32 of a handle 16, a handle can include structure that allows for a compressible member to be positioned within the handle in the opposite configuration. For example, the body of the first member of a handle can define a recess that extends from the second end toward the first end that is sized and configured to receive the second end of a compressible member (e.g., has a structural arrangement that mirrors the first recess 52 defined by the second member 32) and the body of the second member of the handle can define a first recess that extends from the first end toward the second end that is sized and configured to receive the first end of the compressible member (e.g., has a structural configuration that mirrors the recess 42 defined by the first member 30). In addition, while the compressible member 18 has been illustrated as having a first arm 74, a second arm 76, a third arm 78, and a fourth arm 80 and each arm has been illustrated as defining a triangular prismatic notch 94 and a triangular prismatic projection 96, a compressible member can include any suitable number of arms and the notch and/or projection of an arm can have any suitable structural arrangement. Examples of numbers of arms considered suitable for a compressible member to define include one, at least one, two, a plurality, three, four, five, six, and any other number considered suitable for a particular embodiment. Examples of structural configurations considered suitable for a notch and/or projection included on an arm include triangular prisms, rectangular prisms, cubes, partial cylinders, and any other structural configuration considered suitable for a particular embodiment. Alternatively, a compressible member can omit the inclusion of a notch and/or projection on each arm or one or more arms defined by the compressible member.

Figure 6:
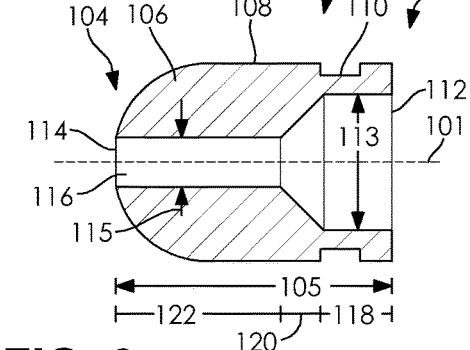
FIG. 6 is a sectional view of the cap of the rotatable control handle illustrated in FIG. 1 taken along the lengthwise axis of the cap.

In the illustrated embodiment, the cap 20 is rotatably attached to the handle 16 and, as illustrated in FIG. 6, has a lengthwise axis 101, a first end 102, a second end 104, a length 105, and a body 106 that defines an exterior surface 108, a recess 110, a first opening 112, a second opening 114, and a passageway 116. The length 105 extends from the first end 102 to the second end 104 and is greater than the length of the second recess 54 defined by the second member 32. In the illustrated embodiment, the length 105 of the cap 20 is equal to about 15.7 millimeters and the outside diameter of the cap 20 at the first end 102 is equal to about 11 millimeters. The recess 110 extends into the body 106 of the cap 20 from the exterior surface 108 toward the lengthwise axis 101 of the cap 20 and is sized and configured to receive a portion of the projection 56 defined by the second member 32 such that the cap 20 can be releasably, and rotatably, attached to the handle 16 and the cap 20 can rotate relative to the handle 16.

The first opening 112 has a first inside diameter 113 and the second opening 114 has a second inside diameter 115 that is less than the first inside diameter 113. The first inside diameter 113 is equal to about 8 millimeters and the second opening is equal to about 3.2 millimeters. The passageway 116 extends from the first opening 112 to the second opening 114 and has proximal portion 118, an intermediate portion 120, and a distal portion 122. Each of the first opening 112, second opening 114, and passageway 116 is sized and configured to receive the guide member 22 and medical device (e.g., guidewire), as described in more detail herein. The proximal portion 118 has a constant inside diameter that is equal to the first inside diameter 113. The proximal portion 118 has a length that extends from the first end 102 to the intermediate portion 120 that is equal to about 4 millimeters. The distal portion 122 has a constant inside diameter that is equal to the second inside diameter 115. The intermediate portion 120 has a diameter that tapers from the first inside diameter 113 to the second inside diameter 115 and from the proximal portion 118 to the distal portion 122 such that the wall of the intermediate portion 120 is disposed at angle equal to about 45 degrees relative to the lengthwise axis 101. In the illustrated embodiment, the distal portion 122 has a length that is greater than the length of the proximal portion 118 and the length of the intermediate portion 120.

Attachment of the cap 20 to the handle 16 can be accomplished by first inserting the guide member 22 into the passageway 116 defined by the cap 20, then inserting the cannula 24 into the passageway 142 defined by the guide member 22, contacting the first end 102 of the cap 20 to the second end 48 of the second member 32, and applying an axial force on the cap 20 directed toward the second member 32 until the projection 56 defined by the second member 32 is disposed within the recess 110 defined by the cap 20. Alternative embodiments can include a cap that defines a projection that is sized and configured to be received within a recess defined by the second member of a housing. The projection defined by the cap can extend from the exterior surface of the cap and away from the lengthwise axis of the cap and the recess defined by the second member can extend from an interior surface of the second member and away from the lengthwise axis of the second member.

While the cap 20 has been illustrated as having a particular structural configuration and having particular dimensions, a cap included in a rotatable control handle can have any suitable structural configuration and can have any suitable dimensions. Selection of a suitable structural configuration and dimensions for a cap can be based on various considerations, such as the structural configuration of a handle included in the rotatable control handle and/or the material(s) that forms the medical device on which the rotatable control handle is intended to be disposed. In addition, while the cap 20 has been illustrated as being attached to the handle 16 using a snap fit configuration, a cap can be releasably attached to a handle using any suitable technique or method of attachment considered suitable for a particular embodiment. Selection of a suitable technique or method of attachment between a cap and a handle can be based on various considerations, such as the material(s) that forms the handle to which the cap is intended to be attached. Examples of techniques and methods of attachment considered suitable between a cap and a handle include snap fit configurations, threaded connections (e.g., a second member of the handle defines threads that are sized and configured to mate with threads defined by a cap), fusing, welding, using adhesives, and any other technique or method of attachment considered suitable for a particular embodiment. For example, a cap can be fixedly attached to a handle (e.g., using adhesive, fusing) such that it is not rotatable relative to the handle. In this alternative embodiment, only the cannula is rotatable relative to the cap and handle or a combination of the cannula and the guide member is rotatable relative to the cap and the handle.

Figure 7:
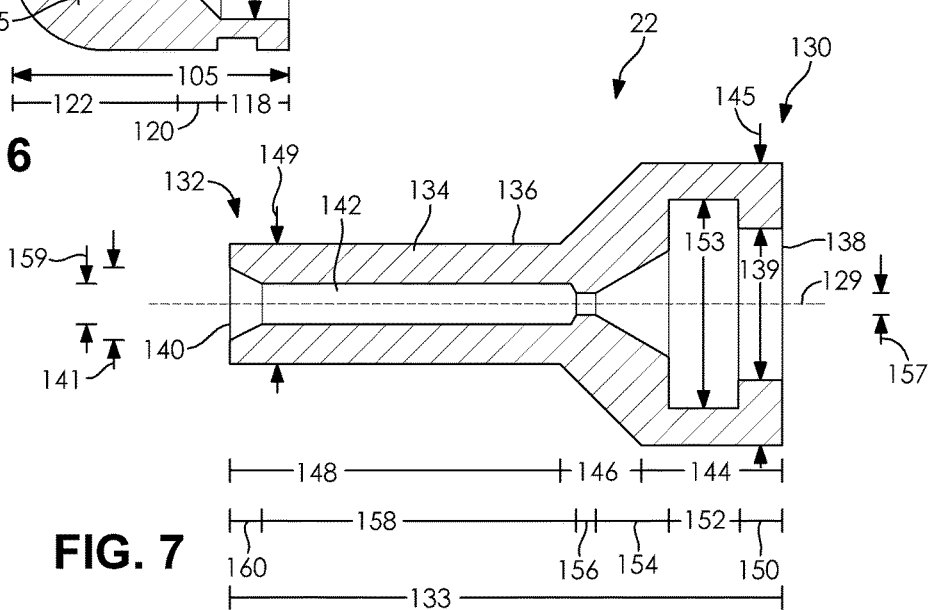
FIG. 7 is a sectional view of the guide member of the rotatable control handle illustrated in FIG. 1 taken along the lengthwise axis of the guide member.

As illustrated in FIG. 7, the guide member 22 has a lengthwise axis 129, a first end 130, a second end 132, a length 133, and a body 134 that defines an exterior surface 136, a first opening 138, a second opening 140, and a passageway 142. The length 133 extends from the first end 130 to the second end 132 and is equal to the length 105 of the cap 20. The exterior surface 136 of the guide member 22 has a structural configuration that corresponds to the structural configuration of the passageway 116 defined by the cap 20 such that the guide member 22 can be positioned within the passageway 116 and attached to the cap 20. The exterior surface 136 of the guide member 22 has a proximal portion 144, an intermediate portion 146, and a distal portion 148. The proximal portion 144 has a first outside diameter 145 that is less than the first inside diameter 113 of the passageway 116. In the illustrated embodiment, the first outside diameter 145 is equal to about 7.9 millimeters and the length of the proximal portion 144 that extends from the first end 130 to the intermediate portion 146 is equal to about 3.9 millimeters. The distal portion 148 has a second outside diameter 149 that is less than the second inside diameter 115 of the passageway 116. In the illustrated embodiment, the second outside diameter 149 is equal to about 3.17 millimeters and the sum of the length of the intermediate portion 146 and the distal portion 148 from the proximal portion 144 to the second end 132 is equal to about 11.7 millimeters. The intermediate portion 146 has an outside diameter that tapers from the first outside diameter 145 to the second diameter 149 and from the proximal portion 144 to the distal portion 148. In the illustrated embodiment, the intermediate portion 146 tapers from the proximal portion 144 to the distal portion 148 such that the wall of the intermediate portion 146 is disposed at an angle that is equal to about 45 degrees relative to the lengthwise axis 129 of the guide member 22.

The first opening 138 has a first inside diameter 139 and the second opening 140 has a second inside diameter 141 that is less than the first inside diameter 139. The passageway 142 extends from the first opening 138 to the second opening 140 and has proximal portion 150, a first intermediate portion 152, a second intermediate portion 154, a third intermediate portion 156, a fourth intermediate portion 158, and a distal portion 160. Each of the first opening 138, the second opening 140, and the passageway 142 is sized and configured to receive a portion of the cannula 24 and a medical device, as described in more detail herein. The proximal portion 150 has a diameter equal to the first inside diameter 139, the first intermediate portion 152 has a third inside diameter 153, the second intermediate portion 154 has a diameter that tapers from the first intermediate portion 152 to the third intermediate portion 156, the third intermediate portion 156 has a fourth inside diameter 157, the fourth intermediate portion 158 has a fifth inside diameter 159, and the distal portion 160 has a diameter that increases from the fourth intermediate portion 158 to the second inside diameter 141 at the second end 132 of the guide member 22. The third inside diameter 153 is greater than the first inside diameter 139. The fourth inside diameter 157 is less than the third inside diameter 153 and the fifth inside diameter 159. The fourth inside diameter 157 is sized and configured to allow the cannula 24 to be rotatably disposed through the guide member 22 and the cap 20 and prevent fluid from passing between the guide member 22 and cannula 24 during use.

In the illustrated embodiment, the first inside diameter 139 is equal to about 4.7 millimeters, the second inside diameter 141 is equal to about 2.2 millimeters, the third inside diameter 153 is equal to about 6.2 millimeters, the inside diameter of the second intermediate portion 154 adjacent to the first intermediate portion 152 is equal to about 3.3 millimeters, the fourth inside diameter 157 is equal to about 0.9 millimeters, and the fifth inside diameter 159 is equal to about 1.2 millimeters. In addition, the second intermediate portion 154 tapers from the first intermediate portion 152 to the third intermediate portion 156 such that the wall of the second intermediate portion 154 is disposed at an angle equal to about 30 degrees relative to the lengthwise axis 129. Furthermore, the distal portion 160 increases in diameter from the fourth intermediate portion 158 to the second end 132 such that the wall of the distal portion 160 is disposed at an angle equal to about 30 degrees relative to the lengthwise axis 129. The sum of the lengths of the proximal portion 150 and the first intermediate portion 152 from the first end 130 to the second intermediate portion 154 is equal to about 3.2 millimeters. The length of the first intermediate portion 152 from the proximal portion 150 to the second intermediate portion 154 is equal to about 2 millimeters. The sum of the lengths of the fourth intermediate portion 158 and the distal portion 160 from the third intermediate portion 156 to the second end 132 is equal to about 9.7 millimeters.

In the illustrated embodiment, the guide member 22 is adhesively attached to the cap 20. However, alternative techniques and methods of attachment can be used to attach a guide member to a cap. Examples of techniques and methods of attachment considered suitable between a guide member and a cap included using adhesives, threaded connections, friction fit connections, fusing a portion of the guide member to the cap, forming the guide member as a portion of a cap, snap fit configurations, and any other technique or method of attachment considered suitable for a particular embodiment. For example, alternative embodiments can include a guide member that is rotatably attached to a cap. While the guide member 22 has been illustrated as having a particular structural configuration and having particular dimensions, a guide member included in a rotatable control handle can have any suitable structural configuration and can have any suitable dimensions. Selection of a suitable structural configuration and dimensions for a guide member can be based on various considerations, such as the structural configuration of a cap included in the rotatable control handle and/or the material(s) that forms the medical device on which the rotatable control handle is intended to be disposed. Alternative embodiments can omit the inclusion of a guide member and a cap can define structure that is sized and configured to correspond with a portion of the structure of a cannula.

While the guide member 22 has been illustrated as having a proximal portion 144 that has a first outside diameter 145 that is less than the first inside diameter 113 of the passageway 116 defined by the cap 20 and a distal portion 148 that has a second outside diameter 149 that is less than the second inside diameter 115 of the passageway 116 defined by the cap 20, a guide member can have any suitable structural arrangement. For example, a guide member can have a proximal portion that has a first outside diameter that is equal to, or greater than, the first inside diameter of the passageway defined by a cap and/or a distal portion that has a second outside diameter that is equal to, or greater than, the second inside diameter of the passageway defined by a cap such that the guide member can be attached to the cap using a friction fit.

Figure 8:
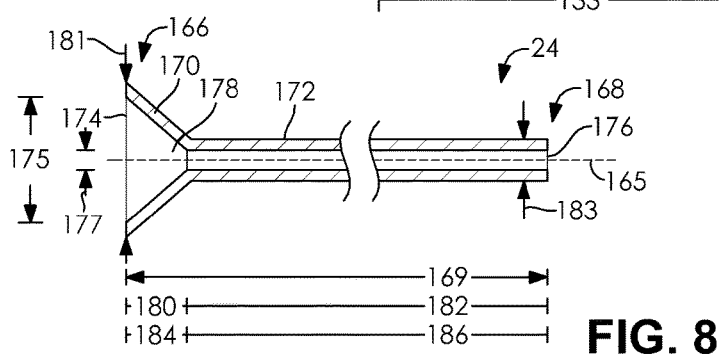
FIG. 8 is a sectional view, partially broken away, of the cannula of the rotatable control handle illustrated in FIG. 1 taken along the lengthwise axis of the cannula.

As illustrated in FIG. 8, the cannula 24 has a lengthwise axis 165, a first end 166, a second end 168, a length 169, and a body 170 that defines an exterior surface 172, a first opening 174, a second opening 176, and a passageway 178. The length 169 extends from the first end 166 to the second end 168 and is sized and configured to pass through a portion of the guide member 22, cap 20, and through a medical device, such as a valve device (e.g., hemostatic valve, introducer). A portion of the exterior surface 172 of the cannula 24 has a structural configuration that corresponds to a portion of the structural configuration of the passageway 142 defined by the guide member 22 such that the cannula 24 can be positioned, and rotate, within the guide member 22. The exterior surface 172 of the cannula 24 has a proximal portion 180 and a distal portion 182. The proximal portion 180 has a first outside diameter 181 that is greater than the fourth inside diameter 157 of the passageway 142 defined by the guide member 22. The distal portion 182 has a second outside diameter 183 that is less than the first outside diameter 181 and is sized and configured to be passed through the third intermediate portion 156 of the passageway 142 defined by the guide member 22. Thus, the second outside diameter 183 is less than the fourth inside diameter 157. This structural arrangement provides a mechanism for passing the cannula 24 through the passageway 142 defined by the guide member 22 until the exterior surface 172 of the cannula 24 along the proximal portion 180 contacts the interior surface of the guide member 22 along the second intermediate portion 154. Alternatively, the second outside diameter of a cannula can be equal to the fourth inside diameter of a guide member such that a friction fit between the cannula and guide member can be accomplished.

The first opening 174 has a first inside diameter 175 and the second opening 176 has a second inside diameter 177 that is less than the first inside diameter 175. The passageway 178 extends from the first opening 174 to the second opening 176 and has proximal portion 184 and a distal portion 186. Each of the first opening 174, second opening 176, and passageway 178 is sized and configured to receive a portion of a medical device, such as a guidewire. The inside diameter of the proximal portion 184 tapers from the first inside diameter 175 at the first opening 174 to the second inside diameter 177 along a portion of the length 169 of the cannula 24.

In the illustrated embodiment, when assembled, as illustrated in FIG. 1, the length of the rotatable control handle 10 from the first end 12 to the second end 14 is equal to about 9 centimeters. In addition, the cap 20 is rotatable relative to the handle 16 and the cannula 24 is rotatable relative to the cap 20 and the handle 16. This arrangement provides a mechanism for allowing a first medical device, such as a guidewire, that has been passed through and attached to the rotatable control handle 10, to be passed through a second medical device, such as a valve device (e.g., hemostatic valve, introducer), such that the first medical device can be rotated relative to the second medical device during use. For example, when delivering an embolization coil, a delivery system that includes a guidewire on which the embolization coil is attached can be attached to the rotatable control handle 10 such that the rotatable control handle 10 is attached to the guidewire between the embolization coil and the proximal end of the guidewire. Subsequently, the rotatable control handle 10 and the attached guidewire can be advanced through a valve device such that the cannula 24 of the rotatable control handle 10 contacts a portion of a valve member attached to the valve device and is partially disposed through the valve member. The handle 16 and guidewire can then be rotated relative to the valve device since the friction applied by the valve member on the cannula 24 of the rotatable control handle 10 maintains the position of the cannula 24. Depending on the structural configuration of a rotatable control handle, a cap and cannula can rotate relative to the valve device during use (e.g., in embodiments in which the guide member and/or cap are attached (e.g., soldered) to a cannula).

In use, the rotatable control handle 10 is positioned on a medical device and attached to the medical device such that the rotatable control handle provides a mechanism for manipulating the position of the medical device during use. The rotatable control handles described herein can be used in combination with, and attached to, any suitable medical device and selection of a suitable medical device to use in combination with a rotatable control handle can be based on various considerations, such as the procedure intended to be performed by the medical device. For example, a rotatable control handle according to an embodiment can be attached to a guidewire, embolization device, probe, lithotripsy probe, delivery device, delivery systems that include a guidewire with an attached embolization coil, embolization coil delivery device, an optic, fiber optic, fiber, laser fiber, suction device, irrigation device, basket, stone basket, grasper, forceps, grasping forceps, drill, catheter, balloon catheter, and any other medical device considered suitable for a particular embodiment.

Each of the handle 16 (e.g., first member 30, second member 32), compressible member 18, cap 20, guide member 22, and cannula 24 can be formed of any suitable material and can be fabricated using any suitable method or technique. Selection of a suitable material to form a handle, compressible member, cap, guide member, and/or cannula and a suitable method or technique to fabricate a handle, compressible member, cap, guide member, and/or cannula according to a particular embodiment can be based on various considerations, including the material(s) that forms a medical device that is intended to be used with a rotatable control handle of which the handle, compressible member, cap, guide member, and/or cannula is a component. Examples of materials considered suitable to form a handle, compressible member, cap, guide member, and/or cannula include biocompatible materials, materials that can be made biocompatible, metals such as stainless steel, titanium, brass, nickel-titanium alloys (e.g., Nitinol), polymers, Pebax (Pebax is a registered trademark of AtoChimie Corporation of Allee des Vosges, Courbevoie, France), nylon, polyethylene, polyurethane, silicone, combinations of the materials described herein, and any other material considered suitable for a particular application. Examples of methods and techniques considered suitable to fabricate a handle, compressible member, cap, guide member, and/or cannula include extrusion processes, molding processes, injection molding processes, casting processes, and any other method or technique considered suitable for a particular embodiment.

In the illustrated embodiment, each of the handle 16 (e.g., first member 30, second member 32), the cap 20, and the guide member 22 is formed of a polymer and each of the compressible member 18 and cannula 25 is formed of a metal. However, in alternative embodiments, a handle can be formed of a first material (e.g., metal) and a compressible member can be entirely formed, or partially formed, of a second material (e.g., polymer) such that the compressible member is relatively more flexible than the handle. This alternative arrangement provides a mechanism for preventing damage to a medical device (e.g., guidewire) that is disposed through the compressible member and the handle.

Figure 9:
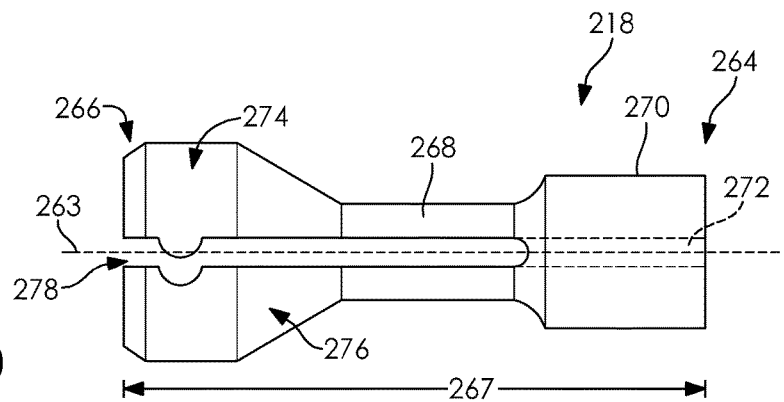
FIG. 9 is an elevation view of an alternative compressible member that can be included in a rotatable control handle.

FIG. 9 illustrates an alternative compressible member 218 suitable for use in a rotatable control handle according to an embodiment. The compressible member 218 is similar to the compressible member 18 illustrated in FIGS. 1, 2, 3, 5, 5A, 5B, 5C, and 5D, and described above, except as detailed below. The compressible member 218 has a lengthwise axis 263, a first end 264, a second end 266, a length 267, and a body 268 that defines a base 270, a passageway 272, a first arm 274, a second arm 276, and a third arm 278.

In the illustrated embodiment, the base 270 is formed of a first material and each of the first arm 274, second arm 276, and third arm 278 is formed of a second material that is different than the first material. The second material is relatively more flexible than the first material such that damage to a medical device disposed through the compressible member 218 is prevented during use. Alternative to, or in combination with, forming each of the arms of a compressible member of a material that is different than the material that forms the base of the compressible member, a compressible member, such as one that is entirely formed of the same material, can include a localized coating on each of the arms that is disposed on a surface that is directed toward the lengthwise axis of the compressible member (e.g., surfaces that are intended to contact a medical device, such as a guidewire). For example, the coating can be disposed on each arm on any surface that contacts a medical device positioned through the compressible member when the compressible member is in the second configuration. The coating can be formed of a material that is different than the material that forms the compressible member and be relatively more flexible than the material that forms the compressible member. Examples of materials considered suitable to form a coating include polymers, rubber, metals, alloys, and any other material considered suitable for a particular embodiment.

Figure 10:
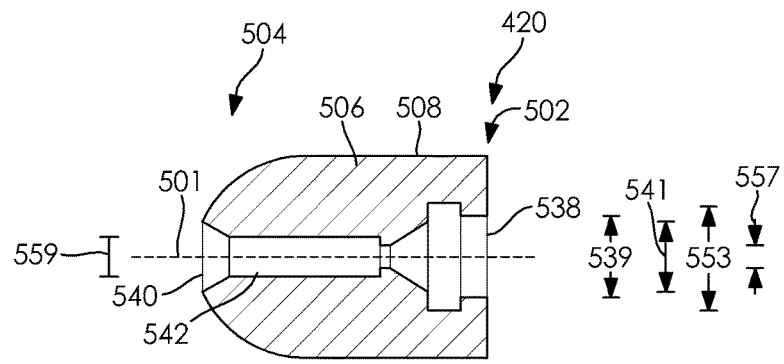
FIG. 10 is a sectional view of an alternative cap that can be included in a rotatable control handle taken along the lengthwise axis of the cap.

FIG. 10 illustrates an alternative cap 420 suitable for use in a rotatable control handle according to an embodiment. The cap 420 is similar to the cap 20 illustrated in FIGS. 1, 2, 3, and 6, and described above, except as detailed below. In the illustrated embodiment, the cap 420 forms a structural configuration similar to the guide member 22, illustrated in FIGS. 1, 2, 3, and 7, and described above. The cap 420 comprises a lengthwise axis 501, a first end 502, a second end 504, a length 505, and a body 506 that defines an exterior surface 508, a first opening 538, a second opening 540, and a passageway 542.

In the illustrated embodiment, the cap 420 omits the inclusion of a recess (e.g., 110) and can be fixedly attached to a handle using an adhesive. The first opening 538 has a first inside diameter 539 and the second opening 540 has a second inside diameter 541 that is less than the first inside diameter 539. The passageway 542 extends from the first opening 538 to the second opening 540 and has proximal portion 550, a first intermediate portion 552, a second intermediate portion 554, a third intermediate portion 556, a fourth intermediate portion 558, and a distal portion 560. Each of the first opening 538, the second opening 540, and the passageway 542 is sized and configured to receive a portion of a cannula and a medical device, such as a guidewire, as described in more detail herein. The proximal portion 550 has a diameter equal to the first inside diameter 539, the first intermediate portion 552 has a third inside diameter 553, the second intermediate portion 554 has a diameter that tapers from the first intermediate portion 552 to the third intermediate portion 556, the third intermediate portion 556 has a fourth inside diameter 557, the fourth intermediate portion 558 has a fifth inside diameter 559, and the distal portion 560 has a diameter that increases from the fourth intermediate portion 558 to the second inside diameter 541 at the second end 504 of the cap 420. The third inside diameter 553 is greater than the first inside diameter 539. The fourth inside diameter 557 is less than the third inside diameter 553 and the fifth inside diameter 559. The fourth inside diameter 557 is sized and configured to allow a cannula to be passed through the cap 420 such that it is rotatably attached to the cap 420.

Methods of using a rotatable control handle are described herein. While the methods described herein are shown and described as a series of acts, it is to be understood and appreciated that the methods are not limited by the order of acts described and illustrated, as some acts may in accordance with these methods, be omitted, be repeated, or occur in different orders and/or concurrently with other acts described herein. While some steps, optional steps, and/or alternative steps are exemplified by using a rotatable control handle on a guidewire, the methods, steps, optional steps, and/or alternative steps described herein can be used on any suitable medical device and to perform any suitable method of using a rotatable control handle, or method of treatment. Selection of a suitable structure on which to use a rotatable control handle according to an embodiment and perform the methods, steps, optional steps, and/or alternative steps described herein can be based on various considerations, such as the method of using a rotatable control handle, or method of treatment, intended to be performed.

Figure 11:
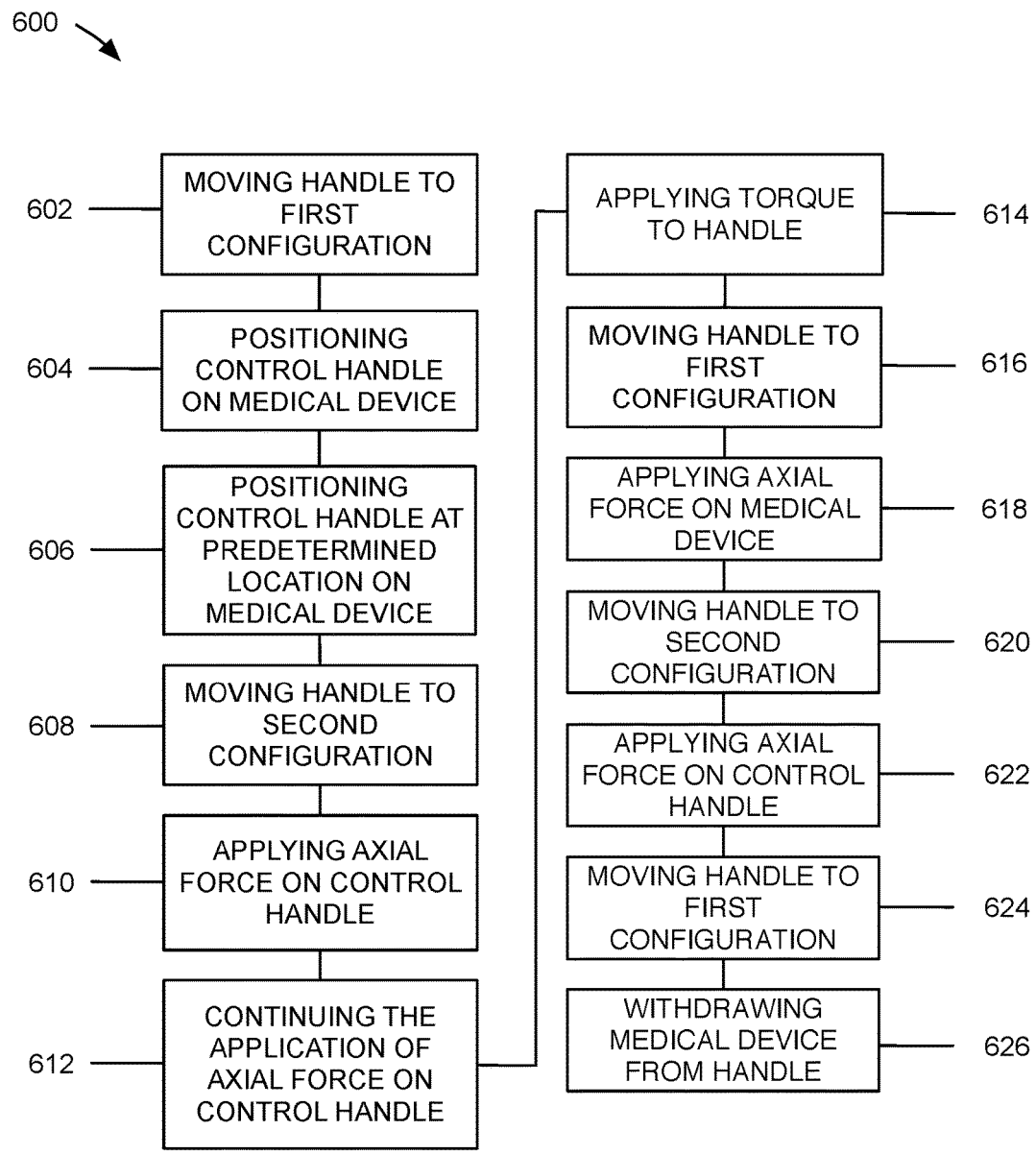
FIG. 11 is a schematic illustration of an example method of using a rotatable control handle.

FIG. 11 is a schematic illustration of an example method 600 of using a rotatable control handle.

A step 602 comprises moving the handle of a rotatable control handle from a second configuration to a first configuration. Another step 604 comprises positioning the rotatable control handle on a medical device. The medical device comprises a first end, a second end, and a length that extends from the first end to the second end. Another step 606 comprises positioning the rotatable control handle at a predetermined location on the medical device. Another step 608 comprises moving the handle of the rotatable control handle from a first configuration to a second configuration. Another step 610 comprises applying an axial force on the rotatable control handle directed toward a valve device such that the medical device is advanced through a valve member of the valve device and the first end of the medical device is disposed on a first side of the valve member and the second end of the medical device is disposed on a second side of the valve member. The valve device comprises a housing, a valve member, and a sheath. Another step 612 comprises continuing the application of an axial force on the rotatable control handle such that the rotatable control handle and the medical device are advanced through the valve member of the valve device and the first end of the cannula is disposed on the second side of the valve member and the second end of the cannula is disposed on the first side of the valve member. Another step 614 comprises applying torque to the handle of the rotatable control handle such that the handle and medical device rotate relative to the valve device. Another step 616 comprises moving the handle of the rotatable control handle from a second configuration to a first configuration. Another step 618 comprises applying axial force on the medical device such that the medical device moves relative to the handle. Another step 620 comprises moving the handle of the rotatable control handle from a first configuration to a second configuration. Another step 622 comprises applying an axial force on the rotatable control handle directed away from the valve device such that the rotatable control handle and the medical device are withdrawn from the valve member of the valve device, the second end of the cannula is disposed on the second side of the valve member, and the medical device and rotatable control handle are free of the valve device. Another step 624 comprises moving the handle of the rotatable control handle from the second configuration to the first configuration. Another step 626 comprises withdrawing the medical device from the first member and the second member of the handle of the rotatable control handle.

Step 602 can be accomplished using any suitable rotatable control handle according to an embodiment, such as rotatable control handle 10, variations thereof, and any other rotatable control handle considered suitable for a particular method of using a rotatable control handle or method of treatment. An example rotatable control handle that can be used to accomplish the methods, steps, alternative steps, and/or optional steps described herein is illustrated and described with respect to FIGS. 1, 2, 3, 4, 5, 5A, 5B, 5C, 5D, 6, 7, and 8, and comprises a handle 16, a compressible member 18, a cap 20, a guide member 22, and a cannula 24.

Step 602 can be accomplished by applying torque on the first member 30 while maintaining the position of the second member 32 such that the second end 36 of the first member 30 advances away from the second end 48 of the second member 32, the first member 30 becomes free of the second member 32, and the compressible member 18 moves from the second configuration to the first configuration. Alternatively, step 602 can be accomplished by applying torque on the first member 30 while maintaining the position of the second member 32 until the second end 36 of the first member 30 advances away from the second end 48 of the second member 32 and the compressible member 18 moves from the second configuration to the first configuration while the first member 30 and second member 32 are still in contact with one another. For example, in the second configuration the first member first end is disposed a first distance from the second member second end and in the first configuration the first member first end first end is disposed a second distance from the second member second end that is greater than the first distance. Alternatively, step 602 can be accomplished by applying torque on the second member 32 while maintaining the position of the first member 30 such that the second end 48 of the second member 32 advances away from the second end 36 of the first member 30, the first member 30 becomes free of the second member 32, and the compressible member 18 moves from the second configuration to the first configuration. Alternatively, step 602 can be accomplished by applying torque on the second member 32 while maintaining the position of the first member 30 until the second end 48 of the second member 32 advances away from the second end 36 of the first member 30 and the compressible member 18 moves from the second configuration to the first configuration while the first member 30 and second member 32 are still in contact with one another. Alternatively, step 602 can be accomplished by applying torque on the second member 32 while concurrently applying torque on the first member 30 such that the second end 48 of the second member 32 advances away from the second end 36 of the first member 30, the first member 30 becomes free of the second member 32, and the compressible member 18 moves from the second configuration to the first configuration. Alternatively, step 602 can be accomplished by applying torque on the second member 32 while concurrently applying torque on the first member 30 until the second end 48 of the second member 32 advances away from the second end 36 of the first member 30 and the compressible member 18 moves from the second configuration to the first configuration while the first member 30 and second member 32 are still in contact with one another. Alternatively, step 602 can be omitted from method 600 if the rotatable control handle 10 is provided in the first configuration.

Figure 12:
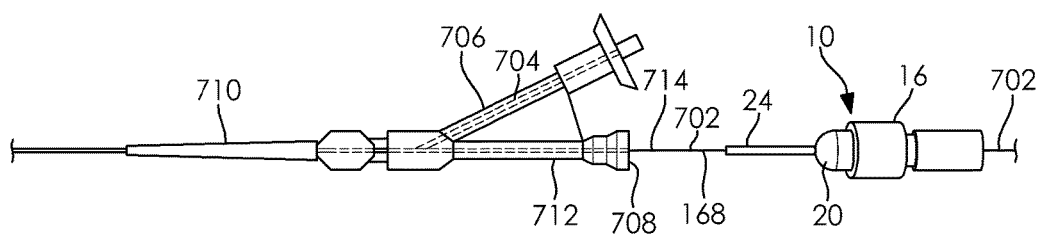
FIG. 12 is a partial elevation view of a rotatable control handle attached to a guidewire. The guidewire is partially disposed through a valve device.
Figure 13:
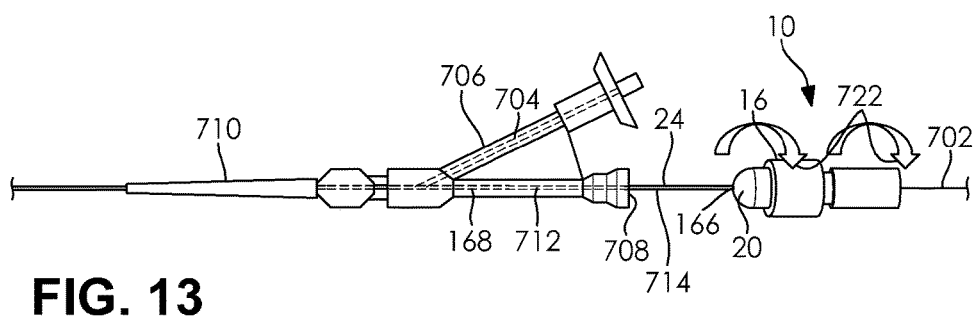
FIG. 13 is a partial elevation view of a rotatable control handle attached to a guidewire. The guidewire and the cannula of the rotatable control handle are partially disposed through a valve device.

Step 604 can be accomplished by positioning the rotatable control handle 10 on any suitable medical device and selection of a suitable medical device to use in combination with a rotatable control handle can be based on various considerations, such as the method of using a rotatable control handle or method of treatment intended to be performed. Example medical devices on which it is considered suitable to position a rotatable control handle include guidewires, embolization devices, probes, lithotripsy probes, delivery devices, delivery systems that include a guidewire with an attached embolization coil, optics, fiber optics, fibers, laser fibers, suction devices, irrigation devices, baskets, stone baskets, graspers, forceps, grasping forceps, drills, catheters, balloon catheters, and any other device considered suitable for a particular application. It is considered advantageous to position a rotatable control handle on a medical device at least because it provides a mechanism for providing fine motor control over the medical device, it provides a mechanical stop to the distal advancement of the medical device through a second medical device (e.g., valve device, hemostatic valve), and provides a mechanism for manipulating the medical device through a second medical device (e.g., valve device, hemostatic valve) through which it is disposed. For example, if a medical device 702 is advanced through a valve device 704, as shown in FIGS. 12 and 13, the cannula 24 of the rotatable control handle 10 will contact the valve member 708 of the valve device 704 instead of the medical device 702 to prevent damage (e.g., kinking) to the medical device 702 during use and increase the maneuverability of the medical device 702 through the valve member 708. When the method 600 of using a rotatable control handle is being performed as part of a method of treatment, it is considered advantageous to position a rotatable control handle on a medical device at least because it provides a mechanism for providing fine motor control over the medical device, it provides a mechanical stop to the distal advancement of the medical device within a bodily passage, and provides a mechanism for manipulating the medical device through a second medical device (e.g., valve device, hemostatic valve) through which it is disposed. In embodiments in which a rotatable control handle is positioned on a guidewire, the rotatable control handle can be positioned on any suitable guidewire, formed of any suitable material and having any suitable structural arrangement, and selection of a suitable guidewire can be based on various considerations, such as the treatment intended to be performed. Examples of materials considered suitable to form a guidewire disposed through a rotatable control handle include guidewires that are formed of biocompatible materials, materials that can be made biocompatible, metals such as stainless steel, titanium, brass, nickel-titanium alloys (e.g., Nitinol), polymers, Pebax, nylon, polyethylene, polyurethane, silicone, combinations of the materials described herein, and any other material considered suitable for a particular embodiment.

Step 604 can be accomplished by applying an axial force on a medical device directed toward the rotatable control handle 10 while maintaining the position of the handle 16 such that the first end or second end of the medical device is advanced through the passageway 40 and recess 42 defined by the first member 30, the passageway 72 defined by compressible member 18, between the arms 74, 76, 78, 80 of the compressible member 18, the first recess 52, second recess 54, and passageway 58 defined by the second member 32, the passageway 142 defined by the guide member 22, and the passageway 178 defined by the cannula 24. Alternatively, step 604 can be accomplished by maintaining the position of the medical device and applying an axial force on the first member 30 and second member 32 of the rotatable control handle 10 directed toward the medical device such that the first end or second end of the medical device is advanced through the passageway 40 and recess 42 defined by the first member 30, the passageway 72 defined by the compressible member 18, between the arms 74, 76, 78, 80 of the compressible member 18, the first recess 52, second recess 54, and passageway 58 defined by the second member 32, the passageway 142 defined by the guide member 22, and the passageway 178 defined by the cannula 24. Alternatively, in embodiments that omit the inclusion of a guide member, the medical device is passed through the passageway defined by a cap and into the passageway defined by the cannula.

Step 606 can be accomplished based upon various measured factors, and selection of a suitable measurement to base the positioning of a rotatable control handle on a medical device according to a particular embodiment can be based on various considerations, including the method of using a rotatable control handle intended to be performed. Examples of measurements considered suitable to base the positioning of a rotatable control handle on a medical device include the structural arrangement of a second medical device (e.g., valve device, hemostatic valve), an estimate as to the length of the medical device desired to be passed through a second medical device (e.g., valve device, hemostatic valve), and any other measurement considered suitable for a particular application. Alternatively, a rotatable control handle can be positioned on a medical device at any suitable location between the first end and the second end of the medical device. When the method 600 of using a rotatable control handle is being performed as part of a method of treatment, step 606 can alternatively be accomplished based upon various measured and/or physiological factors, and selection of a suitable measurement and/or physiological factor to base the positioning of a rotatable control handle on a medical device according to a particular embodiment can be based on various considerations, including the treatment intended to be performed. Examples of measurements and/or physiological factors considered suitable to base the positioning of a rotatable control handle on a medical device when performing a method of treatment include the structural arrangement of a bodily passage, an estimate as to the length of the medical device desired to be introduced into a bodily passage, the location of a point of treatment within a bodily passage, a previously determined measurement (e.g., the location desired to place an embolization coil within a bodily passage), and any other measurement and/or physiological factor considered suitable for a particular application. Alternative embodiments can omit the inclusion of step 606.

Step 608 can be accomplished by applying torque on the first member 30 while maintaining the position of the second member 32 such that the second end 36 of the first member 30 advances toward the second end 48 of the second member 32, the first member 30 becomes releasably attached to the second member 32, and the compressible member 18 moves from the first configuration to the second configuration. For example, in the first configuration the first member first end is disposed a first distance from the second member second end and in the second configuration the first member first end first end is disposed a second distance from the second member second end that is less than the first distance and the first member is releasably attached to the second member. Alternatively, step 608 can be accomplished by applying torque on the second member 32 while maintaining the position of the first member 30 such that the second end 48 of the second member 32 advances toward the second end 36 of the first member 30, the first member 30 becomes releasably attached to the second member 32, and the compressible member 18 moves from the first configuration to the second configuration. Alternatively, step 608 can be accomplished by applying torque on the first member 30 while concurrently applying torque on the second member 32 such that the second end 48 of the second member 32 advances toward the second end 36 of the first member 30, the first member 30 becomes releasably attached to the second member 32, and the compressible member 18 moves from the first configuration to the second configuration.

Step 610 can be accomplished by applying an axial force on any suitable portion of the rotatable control handle 10 (e.g., handle 16) directed toward the valve device such that the medical device is advanced through the valve member. FIG. 12 illustrates a guidewire 702 positioned through a valve device 704 that has a housing 706, a valve member 708, and a sheath 710 such that the first end of the guidewire 702 is disposed on a first side 712 of the valve member 708 and the second end of the guidewire 702 is disposed on a second side 714 of the valve member 708. In embodiments in which the first end of the guidewire is disposed within the passageway 178 defined by the cannula 24, step 610 can be omitted from method 600.

Alternatively, step 610 can comprise applying an axial force on the medical device directed toward a valve device such that the medical device is advanced through the valve member of the valve device and the first end of the medical device is disposed on a first side of the valve member and the second end of the medical device is disposed on a second side of the valve member. This alternative step can be accomplished by applying an axial force on any suitable portion of the medical device directed toward the valve device such that the medical device is advanced through the valve member. During performance of method 600, the sheath of the valve device can optionally be free of any other device or partially disposed within a third medical device (e.g., model of a bodily passage, such as a model of a venous valve).

While method 600 has been described as a method of using a rotatable control handle, method 600, and the alternative steps and/or optional steps described with respect to method 600, can be accomplished as part of any suitable method that uses a rotatable control handle. For example, method 600, and the alternative steps and/or optional steps described with respect to method 600, can alternatively be used as a method of treatment, or as part of a method of treatment, as a method of demonstrating use of a rotatable control handle, or as part of a method of demonstrating use of a rotatable control handle, as a method of controlling a medical device, or as part of a method of controlling a medical device, as a method of positioning a medical device (e.g., guidewire) within a rotatable control handle, or as part of a method of positioning a medical device (e.g., guidewire) within a rotatable control handle. When the method 600 is being performed as part of a method of treatment, the sheath of the valve device can optionally be partially disposed within a bodily passage or can be entirely disposed outside of a bodily passage. When the method 600 is being performed as part of a method of treatment, optional steps that can be completed comprise creating a surgical opening in a bodily passage (e.g., body vessel) using a needle; applying an axial force on a guidewire directed toward the needle such that the guidewire is passed through a bore of the needle and is partially disposed within the bodily passage; applying an axial force on a valve device directed toward the guidewire such that the valve device is advanced over the guidewire and is partially disposed within the bodily passage, the valve device has a housing, a valve member, a sheath, and a dilator; applying an axial force on the dilator directed away from the bodily passage such that the dilator is removed from the valve device and is free of the guidewire; applying an axial force directed toward a bodily passage on any suitable portion of a valve device such that the sheath is partially disposed within the bodily passage; and/or applying an axial force on the guidewire directed away from the bodily passage such that the guidewire is removed from the valve device and is free of the bodily passage. When the method 600 is being performed as part of a method of treatment, the steps, alternative steps, and/or optional steps described herein can be accomplished with respect to treating any suitable condition within any suitable bodily passage including, but not limited to, a salivary duct, the urinary tract, a portion of the vascular system, an artery, a vein, and any other bodily passage considered suitable for a particular application.

Step 612 can be accomplished by applying an axial force on any suitable portion of the rotatable control handle 10 (e.g., handle 16) directed toward the valve device such that the cannula 24 is advanced through the valve member. FIG. 13 illustrates the cannula 24 of a rotatable control handle 10 positioned through a valve device 704 that has a housing 706, a valve member 708, and a sheath 710 such that the second end 168 of the cannula 24 is disposed on the first side 712 of the valve member 708 and the first end 166 of the cannula 24 is disposed on the second side 714 of the valve member 708. Alternatively, when method 600 is being performed as a method of treatment, step 612 can comprise continuing the application of an axial force on the rotatable control handle such that the rotatable control handle and the medical device are advanced through the valve member of the valve device, the first end of the cannula is disposed on the second side of the valve member, the second end of the cannula is disposed on the first side of the valve member, and the second end of the medical device is disposed at a point of treatment (e.g., the desired location to deliver an embolization coil).

Step 614 can be accomplished by applying a torque on any suitable portion of the rotatable control handle 10 (e.g., handle 16) in a clockwise or counterclockwise direction such that the handle 16 and medical device rotate relative to the valve device. As illustrated in FIG. 13, the application of a force in the counterclockwise direction, as illustrated by arrows 722, will result in rotation of the guidewire 702 and the handle 16 in a counterclockwise direction. Since the cannula 24 is disposed through the valve member 708 of the valve device 704, the position of the cannula 24 will be fixed, or substantially fixed, during rotational movement of the handle 16 and guidewire 702. Optionally, depending on the method of using a rotatable control handle being performed, step 614 can be omitted from method 600. For example, when the method 600 is being performed as part of a method of treatment, the medical device on which the rotatable control is disposed can comprise a delivery system that includes a guidewire with an attached embolization coil disposed on the second end of the guidewire and an optional step that can be included in the method of treatment comprises continuing the application of torque on the handle until the embolization coil has been delivered at a point of treatment. This optional step can be accomplished as described with respect to step 614. Also, when method 600 is being performed as a method of treatment, another optional step comprises confirming placement of the embolization coil. This optional step can be accomplished using any suitable visualization technique or method, such as x-ray, fluoroscopy, and any other visualization technique or method considered suitable for a particular embodiment.

Step 616 can be accomplished as described herein with respect to step 602. Optionally, step 616 can be accomplished while the cannula 24 is disposed through the valve member of a valve device.

Step 618 can be accomplished by applying an axial force on any suitable portion of the medical device directed toward, or away from, the valve device such that the medical device is advanced through, or partially withdrawn from, the valve member. When method 600 is being performed as a method of treatment, an optional step comprises continuing the application of an axial force on the medical device until the second end of the medical device is disposed at a point of treatment. This optional step can be accomplished by applying an axial force on any suitable portion of the medical device directed toward, or away from, the valve device such that the medical device is advanced through, or partially withdrawn from, the valve member and the second end is advanced toward, or positioned at, a point of treatment. Optionally, step 618, and the optional step described above, can be accomplished while the cannula 24 is disposed through the valve member of a valve device. It is considered advantageous to advance, withdraw, and rotate a medical device, such as a guidewire, that is disposed through the valve member of a valve device, or other medical device, through a rotatable control handle that is in contact with the valve member to prevent kinking of the medical device and provide a mechanism to reduce the force required to advance, withdraw, and rotate the medical device. For example, when using a rotatable control handle, a medical device, such as a guidewire, can be advanced, withdrawn, and rotated within a second medical device, such as a valve device, using only one hand.

Step 620 can be accomplished as described herein with respect to step 608. Optionally, step 620 can be accomplished while the cannula 24 is disposed within the valve member.

Alternatively, depending on the method of using a rotatable control handle being performed, each of step 616, step 618, and/or step 620 can be omitted from method 600 or repeated. For example, when method 600 is being performed as a method of treatment, each of step 616, 618, and/or step 620 can be omitted from method 600 or repeated.

Step 622 can be accomplished by applying an axial force on any suitable portion of the rotatable control handle 10 (e.g., handle 16) directed away from the valve device such that the medical device is withdrawn from the valve member. Alternatively, step 622 can comprise applying an axial force on the medical device directed away from the valve device such that the rotatable control handle and medical device are withdrawn from the valve member of the valve device, the second end of the cannula is disposed on the second side of the valve member, and the medical device and rotatable control handle are free of the valve device. This alternative step can be accomplished by applying an axial force on any suitable portion of the medical device directed away from the valve device such that the medical device and rotatable control handle are withdrawn from the valve member.

Step 624 can be accomplished as described herein with respect to step 602. Optionally, step 624 can be omitted from method 600.

Step 626 can be accomplished by applying an axial force on the medical device directed away from the rotatable control handle 10 while maintaining the position of the handle 16 such that the first end or second end of the medical device is withdrawn from the passageway 40 and recess 42 defined by the first member 30, the passageway 72 defined by the compressible member 18, between the arms 74, 76, 78, 80 of the compressible member 18, the first recess 52, second recess 54, and passageway 58 defined by the second member 32, the passageway 142 defined by the guide member 22, and the passageway 178 defined by the cannula 24. Alternatively, step 626 can be accomplished by maintaining the position of the medical device and applying an axial force on the first member 30 and second member 32 of the rotatable control handle 10 directed away from the medical device such that the first end or second end of the medical device is advanced through the passageway 40 and recess 42 defined by the first member 30, the passageway 72 defined by the compressible member 18, between the arms 74, 76, 78, 80 of the compressible member 18, the first recess 52, second recess 54, and passageway 58 defined by the second member 32, the passageway 142 defined by the guide member 22, and the passageway 178 defined by the cannula 24. Alternatively, in embodiments that omit the inclusion of a guide member, the medical device is passed through the passageway defined by a cap and into the passageway defined by the cannula. Optionally, step 626 can be omitted from method 600.

While step 602, step 608, step 616, step 620, and step 624 have been described as being accomplished by applying torque to a portion of a handle, depending on the structural arrangement of a handle of a rotatable control handle, each of these steps can be accomplished by applying an axial force on a portion of a rotatable control handle. For example, in embodiments in which the first member of a handle is releasably attachable to a second member using a snap fit attachment, step 602, step 616, and step 624 can be accomplished by applying an axial force on the first member directed away from the second member while maintaining the position of the second member until the first member is free of attachment to the second member. Alternatively, in embodiments in which the first member of a handle is releasably attachable to a second member using a snap fit attachment, step 602, step 616, and step 624 can be accomplished by applying an axial force on the second member directed away from the first member while maintaining the position of the first member until the first member is free of attachment to the second member. Alternatively, in embodiments in which the first member of a handle is releasably attachable to a second member using a snap fit attachment, step 602, step 616, and step 624 can be accomplished by applying an axial force on the first member directed away from the second member while concurrently applying an axial force on the second member directed away from the first member until the first member is free of attachment to the second member.

In embodiments in which the first member of a handle is releasably attachable to a second member using a snap fit attachment, step 608 and step 620 can be accomplished by applying an axial force on the first member directed toward the second member while maintaining the position of the second member until the first member is releasably attached to the second member. Alternatively, in embodiments in which the first member of a handle is releasably attachable to a second member using a snap fit attachment, step 608 and step 620 can be accomplished by applying an axial force on the second member directed toward the first member while maintaining the position of the first member until the first member is releasably attached to the second member. Alternatively, in embodiments in which the first member of a handle is releasably attachable to a second member using a snap fit attachment, step 608 and step 620 can be accomplished by applying an axial force on the second member directed toward the first member while concurrently applying an axial force on the first member directed toward the second member until the first member is releasably attached to the second member.

Figure 14:
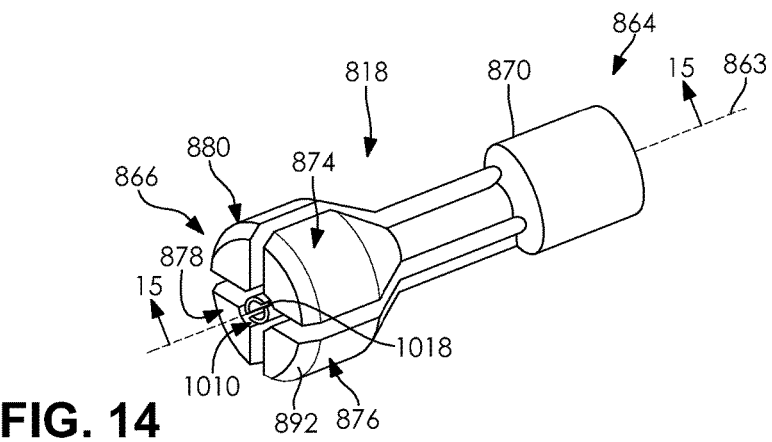
FIG. 14 is a perspective view of another alternative compressible member that can be included in a rotatable control handle.
Figure 15:
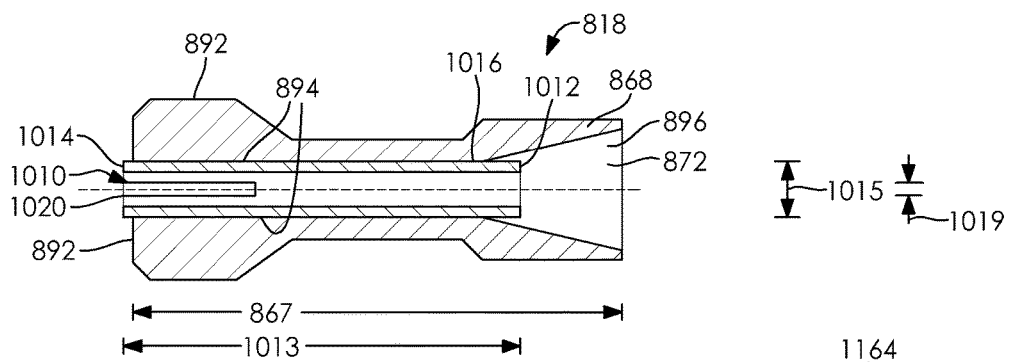
FIG. 15 is a cross-sectional view of the compressible member illustrated in FIG. 14 taken along line 15-15.

FIGS. 14 and 15 illustrate an alternative compressible member 818 suitable for use in a rotatable control handle according to an embodiment. The compressible member 818 is similar to the compressible member 18 illustrated in FIGS. 1, 2, 3, 5, 5A, 5B, 5C, and 5D, and described above, except as detailed below. The compressible member 818 has a lengthwise axis 863, a first end 864, a second end 866, a length 867, and a body 868 that defines a base 870, a passageway 872, a first arm 874, a second arm 876, a third arm 878, and a fourth arm 880.

In the illustrated embodiment, the body 868 of the compressible member 818 defines a continuous surface 894 on the head 892 of each of the arms 874, 876, 878, 880 (e.g., each arm omits a recess and projection), a conical recess 896, and the compressible member 818 includes a inner tubular member 1010 that is formed of a material that is different than the material that forms the compressible member 818. The conical recess 896 extends from the first end 864 toward the second end 866 and provides a mechanism for directing any medical device passed through the compressible member 818 into passageway 872.

The inner tubular member 1010 is partially disposed within the passageway 872 defined by the compressible member 818 and is attached to the compressible member 818 using an adhesive. The inner tubular member 1010 has a first end 1012, a second end 1014, a length 1013 that extends from the first end 1012 to the second end 1014, an outside diameter 1015, and a body 1016 that defines a first notch 1018 and a second notch 1020. The length 1013 of the inner tubular member 1010 is less than the length 867 of the compressible member 818 and the inner tubular member 1010 is partially disposed within passageway 872 such that the first end 1012 is disposed within passageway 872 and the second end 1014 is disposed outside of passageway 872. Each of the notches 1018, 1020 extends from the second end 1014 of the inner tubular member 1010 toward the first end 1012 of the inner tubular member 1010. Each of the notches 1018, 1020 has a width 1019 that is less than the radius of the inner tubular member 1010 and provides a mechanism from moving the inner tubular member 1010 between a first configuration and a second configuration. The inner tubular member 1010 is in the first configuration when the compressible member 818 is in the first configuration and the inner tubular member 1010 is in the second configuration when the compressible member 818 is in the second configuration. In the first configuration, the inner tubular member 1010 has a first inside diameter and in the second configuration the inner tubular member 1010 has a second inside diameter that is less than the first inside diameter.

In the illustrated embodiment, the inner tubular member 1010 is formed of a first material that has a first hardness and the compressible member 818 is formed of a second material that has a second hardness that is greater than the first hardness. For example, the first material can have a first durometer hardness that is less than the durometer hardness of the second material. The inclusion of an inner tubular member having a hardness that is less than the hardness of the compressible member is considered advantageous at least because it provides a mechanism for reducing any damage to a medical device that is disposed through a rotatable control handle that includes compressible member 818.

While the inner tubular member 1010 has been illustrated as being partially disposed within compressible member 818, as being formed of a first material that is different than the second material forming the compressible member 818, as having a particular structural arrangement, and as being attached to the compressible member using an adhesive, an inner tubular member included in a compressible member can be formed of any suitable material, have any suitable structural arrangement, and be attached to a compressible member using any suitable technique or method of attachment. Selection of a suitable material to form an inner tubular member, a structural arrangement for an inner member, and a technique or method of attachment between an inner tubular member and a compressible member can be based on various considerations, including the materials forming a compressible member of which the inner tubular member is a component. Examples of materials considered suitable to form an inner tubular member include biocompatible materials, materials that can be made biocompatible, metals such as stainless steel, titanium, brass, nickel-titanium alloys (e.g., Nitinol), polymers, Pebax, nylon, polyethylene, polyurethane, silicone, combinations of the materials described herein, and any other material considered suitable for a particular application. Examples of suitable lengths of an inner tubular member to position within a passageway defined by a compressible member include partial lengths, entire lengths, and any other length considered suitable for a particular embodiment. Examples of structural arrangements considered suitable for an inner tubular member include arrangements that omit the inclusion of a notch, that include more than two notches, that include one or more notches that extends along a portion of the length of the tubular member, and any other structural arrangement considered suitable for a particular embodiment. Examples of techniques and methods of attachment considered suitable between an inner tubular member and a compressible member include using an adhesive, welding, fusing, and any other technique or method considered suitable for a particular embodiment.

Figure 16:
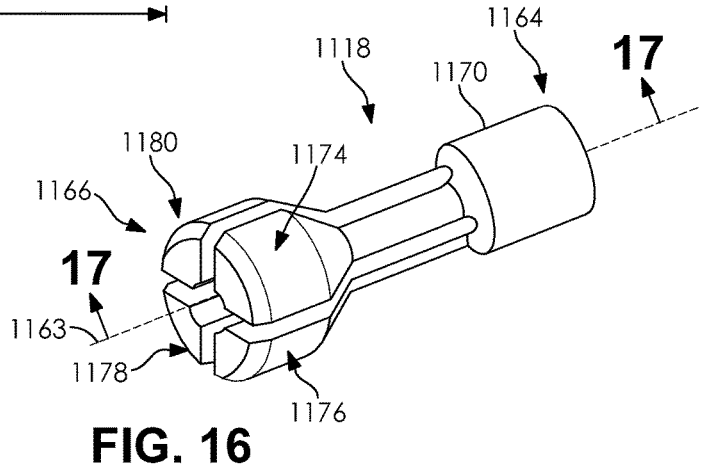
FIG. 16 is a perspective view of another alternative compressible member that can be included in a rotatable control handle.
Figure 17A:
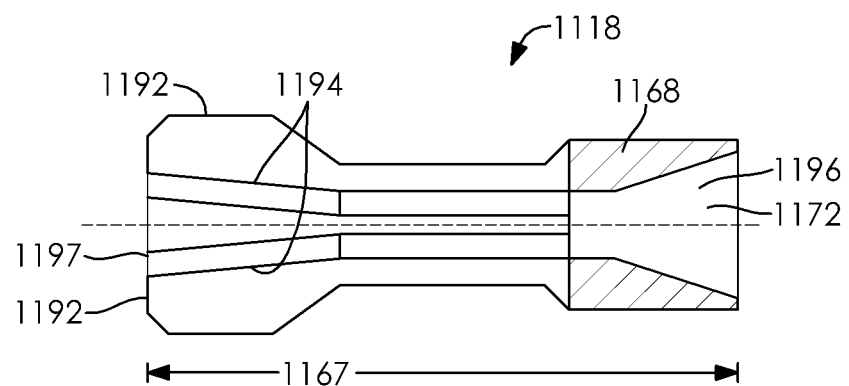
FIG. 17A is a cross-sectional view of the compressible member illustrated in FIG. 16 taken along line 17-17.
Figure 17B:
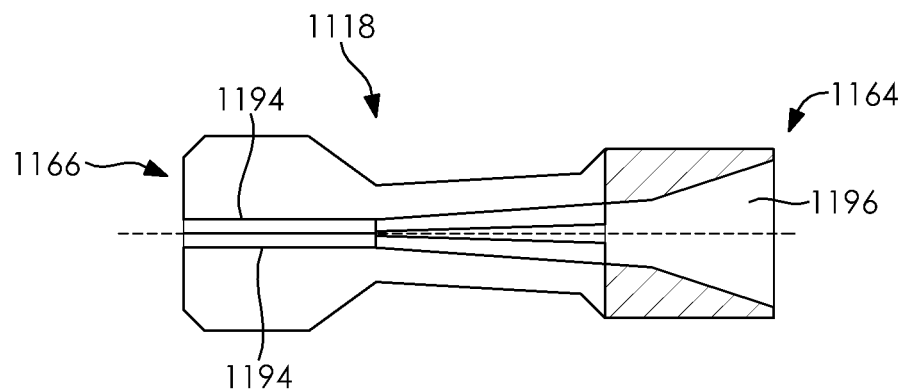
FIG. 17B illustrates the compressible member shown in FIG. 17A in a second configuration.

FIGS. 16, 17A, and 17B illustrate an alternative compressible member 1118 suitable for use in a rotatable control handle according to an embodiment. The compressible member 1118 is similar to the compressible member 1018 illustrated in FIGS. 14 and 15, and described above, except as detailed below. The compressible member 1118 has a lengthwise axis 1163, a first end 1164, a second end 1166, a length 1167, and a body 1168 that defines a base 1170, a passageway 1172, a first arm 1174, a second arm 1176, a third arm 1178, and a fourth arm 1180.

In the illustrated embodiment, the body 1168 of the compressible member 1118 defines a continuous surface 1194 on the head 1192 of each of the arms 1174, 1176, 1178, 1180 (e.g., each arm omits a recess and projection), a first conical recess 1196, and a second conical recess 1197 when the compressible member 1118 is in the first configuration. The first conical recess 1196 extends from the first end 1164 toward the second end 1166 and provides a mechanism for directing any medical device passed through the compressible member 1118 into the passageway 1172. The second conical recess 1197 extends from the second end 1166 toward the first end 1164 and provides a mechanism for increasing the surface area that contacts a medical device passed through the compressible member 1118 during use and when the compressible member 1118 is in the second configuration, as shown in FIG. 17B. The inclusion of a second conical recess 1197 is considered advantageous at least because it increases the fixation between the compressible member 1118 and any medical device disposed through the compressible member 1118, which provides an increase in the amount of torque that can be applied on the medical device during use.

While the compressible member 1118 has been illustrates as having two conical recesses 1196, 1197, a compressible member can include any suitable number of recesses, having any suitable structural arrangement, and formed using any suitable technique. Selection of a suitable number of recesses to include on a compressible member, suitable structural arrangement for a recess, and technique to form a recess can be based on various considerations, including the material that forms the compressible member. Examples of numbers of recess to include on a compressible member include zero, one, at least one, two, a plurality, and any other number of recesses considered suitable for a particular embodiment. Examples of structural arrangements for a recess included on a compressible member include conical, frustoconical, cylindrical, and any other structural arrangement considered suitable for a particular embodiment. An example technique considered suitable to form a recess includes moving a compressible member to the second configuration forming the structure of the recess (e.g., using a drill or other tool) and then allowing the compressible member to return to the first configuration.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A rotatable control handle comprising:
a handle having a first member and a second member releasably attached to the first member, the handle moveable between a first configuration in which the first member is free of attachment to the second member and a second configuration in which the first member is releasably attached to the second member;
a compressible member partially disposed within the first member and the second member and movable between a first configuration when the handle is in the first configuration and a second configuration when the handle is in the second configuration, the compressible member having a compressible member first end, a compressible member second end, and a compressible member body defining a base and a plurality of arms, the plurality of arms extending from the base and cooperatively defining a first inside diameter when the compressible member is in the first configuration and a second inside diameter when the compressible member is in the second configuration, the second inside diameter less than the first inside diameter;
a cap attached to the handle and having a cap first end, a cap second end, and a cap body defining a cap recess and a cap passageway, the cap recess extending into the cap body from the cap first end toward the cap second end, the cap passageway extending from the cap second end to the cap recess and in communication with the cap recess; and
a cannula rotatably attached to the cap and partially disposed within the cap recess and between the second member and the cap, the cannula disposed though the cap passageway and having a cannula first end, a cannula second end, and a cannula body defining a cannula passageway extending from the cannula first end to the cannula second end.

2. The rotatable control handle of claim 1, wherein the first member has a first member first end, a first member second end, and a first member body defining a first member passageway and a first member recess, the first member passageway extending from the first member first end toward the first member second end, the first member recess extending from the first member second end toward the first member first end and in communication with the first member passageway;
wherein the second member has a second member first end, a second member second end, and a second member body defining a second member first recess, a second member second recess, and a second member passageway, the second member first recess extending from the second member first end toward the second member second end, the second member second recess extending from the second member second end toward the second member first end, the second member passageway extending from the second member first recess to the second member second recess and in communication with the second member first recess and second member second recess; and
wherein the compressible member is partially disposed within the first member recess and the second member first recess.

3. The rotatable control handle of claim 2, wherein the first member passageway has a third inside diameter and the first member recess has a fourth inside diameter that is greater than the third inside diameter.

4. The rotatable control handle of claim 2, wherein the second member first recess has a third inside diameter, the second member second recess has a fourth inside diameter, and the second member passageway has a fifth inside diameter that is less than the third inside diameter and the fourth inside diameter.

5. The rotatable control handle of claim 4, wherein the second member passageway has a sixth inside diameter that is less than the fifth inside diameter.

6. The rotatable control handle of claim 2, wherein the second member body defines a second member projection extending into the second member second recess; and
wherein the cap body defines a recess that extends into the cap body that is sized and configured to receive a portion of the second member projection.

7. The rotatable control handle of claim 1, further comprising a guide member disposed between the cannula and the cap, the guide member having a guide member first end, a guide member second end, and a guide member body defining a guide member passageway, the guide member passageway extending from the guide member first end to the guide member second end;
wherein the cannula is partially disposed between the second member and the guide member.

8. The rotatable control handle of claim 7, wherein the guide member passageway has a third inside diameter and a fourth inside diameter that is less than the third inside diameter.

9. The rotatable control handle of claim 1, wherein the plurality of arms comprises a first arm, a second arm, a third arm, and a fourth arm, the compressible member body defining a projection and a notch on each of the first arm, the second arm, the third arm, and the fourth arm.

10. The rotatable control handle of claim 9, wherein the notch defined on the first arm is disposed a first distance from the compressible member second end;
wherein the projection defined on the first arm is disposed a second distance from the compressible member second end; and
wherein the second distance is different than the first distance.

11. The rotatable control handle of claim 1, wherein the cap is rotatably attached to the handle.

12. A rotatable control handle comprising:
a handle having a first member and a second member releasably attached to the first member, the handle moveable between a first configuration in which the first member is free of attachment to the second member and a second configuration in which the first member is releasably attached to the second member, the first member having a first member first end, a first member second end, and a first member body defining a first member passageway and a first member recess, the first member passageway extending from the first member first end toward the first member second end, the first member recess extending from the first member second end toward the first member first end and in communication with the first member passageway, the second member having a second member first end, a second member second end, and a second member body defining a second member first recess, a second member second recess, and a second member passageway, the second member first recess extending from the second member first end toward the second member second end, the second member second recess extending from the second member second end toward the second member first end, the second member passageway extending from the second member first recess to the second member second recess and in communication with the second member first recess and second member second recess;
- a compressible member partially disposed within the first member recess and the second member first recess and movable between a first configuration when the handle is in the first configuration and a second configuration when the handle is in the second configuration, the compressible member having a compressible member first end, a compressible member second end, and a compressible member body defining a base and a plurality of arms, the plurality of arms extending from the base and cooperatively defining a first inside diameter when the compressible member is in the first configuration and a second inside diameter when the compressible member is in the second configuration, the second inside diameter less than the first inside diameter;
- a cap attached to the handle and having a cap first end, a cap second end, and a cap body defining a cap recess and a cap passageway, the cap recess extending into the cap body from the cap first end toward the cap second end, the cap passageway extending from the cap second end to the cap recess and in communication with the cap recess;
- a guide member disposed between the second member and the cap, the guide member having a guide member first end, a guide member second end, and a guide member body defining a guide member passageway, the guide member passageway extending from the guide member first end to the guide member second end; and
- a cannula rotatably attached to the cap and partially disposed within the cap recess and between the second member and the guide member, the cannula disposed through the cap passageway and having a cannula first end, a cannula second end, and a cannula body defining a cannula passageway extending from the cannula first end to the cannula second end.

13. The rotatable control handle of claim 12, wherein the guide member passageway has a third inside diameter and a fourth inside diameter that is less than the third inside diameter.

14. The rotatable control handle of claim 12, wherein the first member passageway has a third inside diameter and the first member recess has a fourth inside diameter that is greater than the third inside diameter.

15. The rotatable control handle of claim 12, wherein the second member first recess has a third inside diameter, the second member second recess has a fourth inside diameter, and the second member passageway has a fifth inside diameter that is less than the third inside diameter and the fourth inside diameter.

16. The rotatable control handle of claim 15, wherein the second member passageway has a sixth inside diameter that is less than the fifth inside diameter.

17. The rotatable control handle of claim 12, wherein the second member body defines a second member projection extending into the second member second recess; and
- wherein the cap body defines a recess that extends into the cap body that is sized and configured to receive a portion of the second member projection.

18. The rotatable control handle of claim 12, wherein the plurality of arms comprises a first arm, a second arm, a third arm, and a fourth arm, the compressible member body defining a projection and a notch on each of the first arm, the second arm, the third arm, and the fourth arm.

19. The rotatable control handle of claim 18, wherein the notch defined on the first arm is disposed a first distance from the compressible member second end;
- wherein the projection defined on the first arm is disposed a second distance from the compressible member second end; and
- wherein the second distance is different than the first distance.

20. A method of using a rotatable control handle, the method comprising the steps of:
- positioning a rotatable control handle on a medical device having a medical device first end and a medical device second end, the rotatable control handle comprising:
  - a handle having a first member and a second member releasably attachable to the first member, the handle moveable between a first configuration in which the first member is free of attachment to the second member and a second configuration in which the first member is releasably attached to the second member;
  - a compressible member partially disposed within the first member and the second member and movable between a first configuration when the handle is in the first configuration and a second configuration when the handle is in the second configuration, the compressible member having a compressible member first end, a compressible member second end, and a compressible member body defining a base and a plurality of arms, the plurality of arms extending from the base and cooperatively defining a first inside diameter when the compressible member is in the first configuration and a second inside diameter when the compressible member is in the second configuration, the second inside diameter less than the first inside diameter;
  - a cap attached to the handle and having a cap first end, a cap second end, and a cap body defining a cap recess and a cap passageway, the cap recess extending into the cap body from the cap first end toward the cap second end, the cap passageway extending from the cap second end to the cap recess and in communication with the cap recess; and
  - a cannula rotatably attached to the cap and partially disposed within the cap recess and between the second member and the cap, the cannula disposed though the cap passageway and having a cannula first end, a cannula second end, and a cannula body defining a cannula passageway extending from the cannula first end to the cannula second end;
- moving the handle of the rotatable control handle from the first configuration to the second configuration such that the rotatable control handle is attached to the medical device;

applying an axial force on the rotatable control handle directed toward a valve device having a housing and a valve member such that the medical device is advanced through the valve member of the valve device and the first end of the medical device is disposed on a first side of the valve member and the second end of the medical device is disposed on a second side of the valve member;

continuing the application of an axial force on the rotatable control handle such that the rotatable control handle and the medical device are advanced through the valve member of the valve device and the first end of the cannula is disposed on the second side of the valve member and the second end of the cannula is disposed on the first side of the valve member; applying torque to the handle of the rotatable control handle such that the handle and medical device rotate relative to the valve device;

moving the handle of the rotatable control handle from the second configuration to the first configuration;

applying axial force on the medical device such that the medical device moves relative to the handle;

moving the handle of the rotatable control handle from the first configuration to the second configuration; and applying an axial force on the rotatable control handle directed away from the valve device such that the rotatable control handle and the medical device are withdrawn from the valve member of the valve device, the second end of the cannula is disposed on the second side of the valve member, and the medical device and rotatable control handle are free of the valve device.

* * * * *